(12) United States Patent
Stenzler

(10) Patent No.: US 6,581,599 B1
(45) Date of Patent: Jun. 24, 2003

(54) METHOD AND APPARATUS FOR DELIVERY OF INHALED NITRIC OXIDE TO SPONTANEOUS-BREATHING AND MECHANICALLY-VENTILATED PATIENTS

(75) Inventor: Alex Stenzler, Orange, CA (US)

(73) Assignee: Sensormedics Corporation, Yorba Linda, CA (US)

( * ) Notice: Subject to any disclaimer, the term of this patent is extended or adjusted under 35 U.S.C. 154(b) by 0 days.

(21) Appl. No.: 09/449,240

(22) Filed: Nov. 24, 1999

(51) Int. Cl.⁷ .............................................. A61M 16/00
(52) U.S. Cl. ......................... 128/204.23; 128/204.22; 128/204.21; 128/204.18; 128/203.12
(58) Field of Search ....................... 128/204.18, 204.21, 128/204.23, 202.22, 203.12, 203.13, 203.22

(56) References Cited

U.S. PATENT DOCUMENTS

| | | | |
|---|---|---|---|
| 5,423,313 A | 6/1995 | Olsson et al. | 128/204.21 |
| 5,485,827 A | 1/1996 | Zapol et al. | 128/200.14 |
| 5,531,218 A | 7/1996 | Krebs | 128/203.12 |
| 5,558,083 A | 9/1996 | Bathe et al. | 128/203.12 |
| 5,651,358 A | 7/1997 | Briend et al. | 128/203.12 |
| 5,692,497 A | * 12/1997 | Schnitzer et al. | 128/204.18 |
| 5,713,349 A | 2/1998 | Keaney | 128/204.23 |
| 5,722,392 A | 3/1998 | Skimming et al. | 128/203.12 |
| 5,732,693 A | * 3/1998 | Bathe et al. | 128/203.12 |
| 5,839,433 A | 11/1998 | Higenbottam | 128/204.2 |
| 5,918,596 A | 7/1999 | Heinonen | 128/204.21 |
| 6,089,229 A | 7/2000 | Bathe et al. | 128/204.21 |
| 6,109,260 A | * 8/2000 | Bathe | 128/203.12 |
| 6,125,846 A | * 10/2000 | Bathe et al. | 128/202.22 |
| 6,142,147 A | * 11/2000 | Head et al. | 128/203.12 |
| 6,158,434 A | * 12/2000 | Lugtigheid et al. | 128/204.22 |
| 6,164,276 A | * 12/2000 | Bathe et al. | 128/202.22 |

FOREIGN PATENT DOCUMENTS

| | | |
|---|---|---|
| EP | 0 640 356 A1 | 3/1995 |
| EP | 0 640 357 A1 | 3/1995 |
| WO | WO 99/49921 | 10/1999 |

OTHER PUBLICATIONS

Norman, C., Keith, C.H., "Nitrogen Oxides In Tobacco Smoke," Nature, vol. 205, No. 4971, pp. 915–916, Feb. 6, 1965.

Contractor, A.M., Snyder, J.M., Fletcher, H.P., Shangraw, R.F., "Development And Evaluation Of An Inhalation Aerosol Of Nitroglycerin," J. Pharm. Sci., vol. 63, No. 6, pp. 907–911, Jun. 1974.

(List continued on next page.)

*Primary Examiner*—Dennis Ruhl
*Assistant Examiner*—Mital Patel
(74) *Attorney, Agent, or Firm*—Sidley Austin Brown & Wood LLP

(57) ABSTRACT

A device and method is disclosed for delivering NO to a patient. The device utilizes a single controller that controls two separate flow controllers to deliver an oxygen-containing gas and a NO-containing gas to the patient. The flow profiles of the oxygen-containing gas and the NO-containing gas are controlled by the controller. In one aspect of the invention, the flow profile of the NO-containing gas is proportional to the flow profile of the oxygen-containing gas throughout patient inspiration. In this regard, the patient receives a steady concentration of NO. In another aspect of the invention, the flow profile of the NO-containing gas is quasi-proportional to the flow profile of the oxygen-containing gas. In this regard, the NO-containing gas flow profile is altered to provide an increased concentration of NO either at the beginning or end of inspiration. In one aspect, the delivery device is used with mechanically-ventilated patients. In the other aspect of the delivery device, the device is used with spontaneously-breathing patients. The device and method, in a preferred embodiment, further contemplates using a gas purge or air flush feature to remove enriched-oxygen and/or NO from the device.

26 Claims, 10 Drawing Sheets

OTHER PUBLICATIONS

Oda, H., Kusumoto, S., Nakajima, T., "Nicrosyl–Hemoglobin Formation In The Blood Of Animals Exposed To Nitric Oxide," Arch Environ Heath, vol. 30, pp. 453–456, Sep. 1975.

Katsuki, S., Arnold, W., Mittal, C., Murad, F., "Stimulation Of Guanylate Cyclase By Sodium Nitroprusside, Nitroglycerin And Nitric Oxide In Various Tissue Preparations And Comparison To The Effects Of Sodium Azide And Hydroxylamine," J Cyclic Nucleotide Res, vol. 3, pp. 23–35 (1977).

Hugod, C., "Effects Of Exposure To 43 ppm Nitric Oxide And 3.6ppm Nitrogen Dioxide On Rabbit Lung," Int Arch Occup Heath, vol. 42, pp. 159–167 (1979).

Yoshia, K., Kasama, K., Kitabatake, M., Okuda, M., Imai, M., "Metabolic Fate Of Nitric Oxide," Int Arch Occup Envron Heath, vol. 46, No. 1, pp. 71–77, Apr. 1980.

Borland, C., Chamberlain, A., Higenbottam, T., "The Fate Of Inhaled Nitric Oxide," Clinical Science, Abstract No. 104, p. 37P (1983).

Demling, R.H., Lalonde, C.C., Jin, L.J., Albes, J., Fiori, N., "The Pulmonary And Systemic Response To Recurrent Endotoxemia In The Adult Sheep," Surgery, vol. 100, No. 5, pp. 876–883, Nov. 1986.

Higenbottam, T., "Primary Pulmonary Hypertension," British Medical Journal, vol. 293, pp. 1456–1457, Dec. 6, 1986.

Higenbottam, T., Wallwork, J., "Primary Pulmonary Hypertension," British Medical Journal, vol. 294, p. 705, Mar. 14, 1987.

Palmer, R.M.J., Ferrige, A.G., Moncada, S., "Nitric Oxide Release Accounts For The Biological Activity Of Endothelium–Derived Relaxing Factor," Nature, vol. 327, pp. 524–526, Jun. 11, 1987.

Ignarro, L.J., Buga, G.M., Wood, K.S., Byrns, R.E., Chaudhuri, G., "Endothelium–Derived Relaxing Factor Produced And Released From Artery And Vein Is Nitric Oxide," Proc Natl Acad Sci USA, vol. 84, No. 24, pp. 9265–9269, Dec. 1987.

Higenbottam, T.W., Pepke–Zaba, J., Scott, J.P., Woolman, P., Coutts, C., Wallwork, J., "Inhaled 'Endothelium–Derived Relaxing Factor' (EDRF) In Primary Hypertension (PPH)," Abstract, Am Rev Respir Dis, vol. 137, No. 4, p. 107, Apr. 1988.

Ignarro, L.J., et al. "Endothelium–Derived Relaxing Factor And Nitric Oxide Possess Identical Pharmacologic Properties As Relaxants Of Bovine Arterial And Venous Smooth Muscle," Journal of Pharmacology and Experimental Therapeutics, vol. 246, No. 1, pp. 218–226, Jul. 1988.

Dinh–Xuan, A.T., Higenbottam, T.W., "Non–Prostanoid Endothelium–Derived Vasoactive Factors," J Int Med Res, vol. 17, pp. 305–315 (1989).

Borland, C.D.R., Higenbottam, T., "A Simultaneous Single Breath Measurement Of Pulmonary Diffusing Capacity With Nitric Oxide and Carbon Monoxide," Eur Respir J, vol. 2, No. 1, pp. 56–63, Jan. 1989.

Buga, G.M., Gold, M.E., Wood, K.S., Chaudhuri, G., Ignarro, L.J., "Endothelium–Derived Nitric Oxide Relaxes Nonvascular Smooth Muscle," European J of Pharmc, vol. 161, No. 1, pp. 61–72, Feb. 14, 1989.

Garg, U.C., Hassid, A., "Nitric Oxide–Generating Vasodilators and 8–Bromo–Cyclic Guanosine Monophosphate Inhibit Mitogenesis And Proliferation Of Cultured Rat Vascular Smooth Muscle Cells," J. Clin. Invest., vol. 83, No. 5, pp. 1774–1777, May 1989.

Meyer, M., Piiper, J., "Nitric Oxide (NO), A New Test Gas For Study Of Alveolar–Capillary Diffusion," Eur. Respir. J., vol. 2, No. 6, pp. 494–496, Jun. 1989.

Dinh Xuan, A.T., Higenbottam, T.W., Scott, J.P., Wallwork, J., "Primary Pulmonary Hypertension: Diagnosis, Medical And Surgical Treatment," Respiratory Medicine, vol. 84, pp. 189–197 (1990).

Moinard, J., Guenard, H., "Determination Of Lung Capillary Blood Volume And Membrane Diffusing Capacity In Patients With COLD Using The NO–CO Method," Eur Respir J, vol. 3, pp. 318–322 (1990).

Archer, S.L., Rist, K., Nelson, D.P., DeMaster, E.G., Cowan, N., Weir, E.K., "Comparison Of The Hemodynamic Effects Of Nitric Oxide And Endothelium–Dependent Vasodilators In Intact Lungs," J Appl. Physiol, vol. 68, No. 2, pp. 735–747, Feb. 1990.

Meyer, M., Schuster, K.D., Schulz, H., Mohr, M., Piiper, J., "Pulmonary Diffusing Capacities For Nitric Oxide And Carbon Monoxide Determined By Rebreathing In Dogs," J Appl Physiol, vol. 68, No. 6, pp. 2344–2357, Jun. 1990.

Vane, J.R., Anggard, E.E., Botting, R.M., "Regulatory Functions Of The Vascular Endothelium," N Engl J Med, vol. 323, No. 1, pp. 27–36, Jul. 5, 1990.

Higenbottam, T., Hay, I., "Has The Treatment Of Asthma Improved?," Chest, vol. 98, No. 3, pp. 706–712, Sep. 1990.

Cremona, G., Dinh–Xuan, A.T., Higenbottam, T.W., "Endothelium–Derived Relaxing Factor And The Pulmonary Circulation," Lung, vol. 169, pp. 185–202 (1991).

Falke, K., Rossaint, R., Pison, U., Slama, K., Lopez, F., Santak, B., Zapol, W.M., "Inhaled Nitric Oxide Selectively Reduces Pulmonary Hypertension In Severe ARDS And Improves Gas Exchange As Well As Right Heart Ejection Fraction—A Case Report," Abstract A248, Am Rev Respir Dis, vol. 143 (1991).

Fratacci, M.D., Frostell, C.G., Chen, T.Y., Wain, J.C., Robinson, D.W., Zapol, W.M., "Inhaled Nitric Oxide—A Selective Pulmonary Vasodilator Of Heparin–Protamine Vasoconstriction In Sheep," Anesthesiology, vol. 75, pp. 990–999 (1991).

Dinh–Xuan, A.T., Higenbottam, T.W., Clelland, C.A., Pepke–Zaba, J., Cremona, G., Butt, A.Y., Large, S.R., Wells, F.C., Wallwork, J., "Impairment Of Endothelium–Dependent Pulmonary–Artery Relaxation In Chronic Obstructive Lung Disease," N Engl J Med, vol. 324, No. 22, pp. 1539–1547, May 30, 1991.

Frostell, C., Fratacci, M.D., Wain, J.C., Jones, R., Zapol, W.M., "Inhaled Nitric Oxide—A Selective Pulmonary Vasodilator Reversing Hypoxic Pulmonary Vasoconstriction," Circulation, vol. 83, No. 6, pp. 2038–2047, Jun. 1991.

Moncada, S., Palmer, R.M.J., Higgs, E.A., "Nitric Oxide: Physiology, Pathophysiology And Pharmacology," Pharmacological Rev, vol. 43, No. 2, pp. 109–142, Jun. 1991.

Frostell, C., Blomquist, H., Lundberg, J., Hedenstierna, G., Zapol, W., Inhaled Nitric Oxide Dilates Human Hypoxic Pulmonary Vasoconstriction Without Causing Systemic Vasodilation, Anesthesiology, Abstract A989, vol. 75, No. 3A, Sep. 1991.

Girard et al., Inhaled Nitric Oxide (NO) In Pulmonary Hypertension Following Mitral Valve Replacement, Abstract A984, vol. 75, No. 3A, Sep. 1991.

Roberts, J.D., Polaner, D.M., Todres, I.D., Lang, P., Zapol, W.M., "Inhaled Nitric Oxide (NO); A Selective Pulmonary Vasodilator For The Treatment Of Persistent Pulmonary Hypertension Of The Newborn," Abstract 1279, Circulation, vol. 84, No. 4, p. II–321, Oct. 1991.

Pepke–Zaba, J., Higenbottam, T.W., Dinh–Xuan, A.T., Stone, D., Wallwork, J., "Inhaled Nitric Oxide As A Cause of Selective Pulmonary Vasodilatation In Pulmonary Hypertension," The Lancet, vol. 338, pp. 1173–1174, Nov. 9, 1991.

Johns, R.A., "EDRF/Nitric Oxide: The Endogenous Nitrovasodilator And A New Cellular Message," Anesthesiology, vol. 75, No. 6, pp. 927–931, Dec. 1991.

Girard, C., Lehot, J.J., Pannetier, J.C., Filley, S., Ffrench, P., Estanove, S., "Inhaled Nitric Oxide After Mitral Valve Replacement In Patients With Chronic Pulmonary Artery Hypertension," Anesthesiology, vol. 77, No. 5 (1992).

Swami, A., Keogh, B.F., "The Injured Lung: Conventional And Novel Respiratory Therapy," Thorax, vol. 47, pp. 555–562 (1992).

Pearl, R.G., The Pulmonary Circulation, Anesthesiology, vol. 5, pp. 848–854 (1992).

Rossaint, R., Falke, K.J., Keitel, M., Slama, K., Gerlach, H., Hahn, M., Zapol, W.M., "Successful Treatment Of Severe Adult Respiratory Distress Syndrome With Inhaled Nitric Oxide," Abstract, Am Rev Respir Dis, vol. 145, No. 4, Part 2, p. A80, Apr. 1992.

Bigatello, L.M., Hurford, W.E., Kacmarek, R.M., Roberts, J.D., Zapol, W.M., "Inhaled Nitric Oxide Is A Selective Pulmonary Vasodilator In Septic Patients With Severe ARDS," Abstract, Am Rev Respir Dis, vol. 145, No. 4, Part 2, p. A185, Apr. 1992.

Rossant et al., "Inhaled Nitric Oxide In Contrast To Infused Prostacyclin Selectively Reduces Pulmonary Hypertension And Improves Gas Exchange In Severe ARDS," Abstract, Am Rev Respir Dis, vol. 145, No. 4, Part 2, p. A185, Apr. 1992.

Snyder, S.H., Bredt, D.S., "Biological Roles Of Nitric Oxide," Sci Am., vol. 266, No. 5, pp. 68–77, May 1992.

Foubert, L., Fleming, B., Latimer, R., Jonas, M., Oduro, A., Borland, C., Higenbottam, T., "Safety Guidelines For Use Of Nitric Oxide," Lancet, vol. 339, No. 8809, pp. 1615–1616, Jun. 27, 1992.

Messent, M., Griffiths, M.J.D., "Pharmacotherapy In Lung Injury," vol. 47, No. 7, pp. 651–656, Jul. 1992.

Barash, P., "Anesthesiology," JAMA, vol. 268, No. 3, pp. 335–337, Jul. 15, 1992.

Dupuy, P.M., Shore, S.A., Drazen, J.M., Frostell, C., Hill, W.A., Zapol, W.M., "Bronchodilator Action Of Inhaled Nitric Oxide In Guinea Pigs," J Clin Invest, vol. 90, pp. 421–428, Aug. 1992.

Kinsella, J.P., McQueston, J., Rosenberg, A.A., Abman, S.H., "Hemodynamic Effects of Exogenous Nitric Oxide In The Ovine Transitional Pulmonary Circulation," Am J Physiol Heart Circ Physiol 32, vol. 32, No. 3, pp. H875–H880, Sep. 1992.

Roberts, J.D., Polaner, D.M., Lang, P., Zapol, W.M., "Inhaled Nitric Oxide In Persistent Pulmonary Hypertension Of The Newborn," The Lancet, vol. 340, pp. 818–819, Oct. 3, 1992.

Kinsella, J.P., Neish, S.R., Shaffer, E., Abman, S.H., "Low–Dose Inhalational Nitric Oxide In Persistent Pulmonary Hypertension Of The Newborn," The Lancet, vol. 340, pp. 819–820, Oct. 3, 1992.

Kacmarek, R.M., "Nitric Oxide As A Bronchodilator In Methacholine Induced Bronchospasm In Mild Asthmatics," Abstract (1993).

Blomquist, H., Wickerts, C.J., Andreen, M., Ullberg, U., Ortquist, A., Frostell, C., "Enhanced Pneumonia Resolution By Inhalation Of Nitric Oxide?," Acta Anaesthesiol Scand, vol. 37, pp. 110–114 (1993).

Higenbottam, T., "Inhaled Nitric Oxide: A Magic Bullet?," Quarterly Journal of Medicine, vol. 86, No. 9, pp. 555–558 (1993).

Rossaint, R., Falke, K.J., Lopez, F., Slama, K., Pison, U., Zapol, W.M., "Inhaled Nitric Oxide For The Adult Respiratory Distress Syndrome," N Engl J Med, vol. 328, pp. 399–405, Feb. 11, 1993.

Pearl, R.G., "Inhaled Nitric Oxide—The Past, The Present and the Future," Anesthesiology, vol. 78, No. 3, pp. 413–416, Mar. 1993.

Higenbottam, T., Rodriguez–Roisin, R., "Highlights On Pulmonary Hypertension: A Commentary," Eur Respir J, vol. 6, No. 7, pp. 932–933, Jul. 1993.

Haworth, S.G., "Pulmonary Hypertension In Childhood," Eur Respir J, vol. 6, No. 7, pp. 1037–1043, Jul. 1993.

Higenbottam, T., Cremona, G., "Acute And Chronic Hypoxic Pulmonary Hypertension," Eur Respir J, vol. 6, No. 8, pp. 1207–1212, Sep. 1993.

O. Stenqvist, et al.; "Evaluation of a New System for Ventilatory Administration of Nitric Oxide;" Acta Anaesthesiologica Scandinavica 1993; pp. 687–691.

Butt, A. Yazdani, Higenbottam, T., "New Therapies For Primary Pulmonary Hypertension," Chest, vol. 105, No. 2, pp. 21S–25S, Feb. 1994.

Foubert, L., Fleming, B., Husain, D., Oduro, A., Cremona, G., Higenbottam, T.W., Latimer, R.D., "Nitric Oxide In Pulmonary Hypertension: Therapeutic Considerations," J Cardio Vasc Anesth, vol. 8, No. 3, Suppl. 2, Abstract No. 41, Jun. 1994.

Snow, D., Gray, S., Ghosh, S., Foubert, L., Cremona, G., Higenbottam, T.W., Wells, F.C., Oduro, A., Latimer, R.D., "Inhaled Nitric Oxide In Pulmonary Hypertension," J Cardio Vasc Anesth, vol. 8, No. 3, Suppl. 2, Abstract No. 127, Jun. 1994.

J.D. Young; "A Universal Nitric Oxide Delivery System;" British Journal of Anaesthesia, vol. 73, No. 4, Oct. 1994; 4 pages.

Jens–Uwe Hagenah; "The Use of Nitric Oxide (NO) in Intensive Care Ventilation;" Dragerwerk Aktiengesellschaft pp. 1 & 3–36.

Higenbottam, T., Butt, Y., "The Treatment Of Primary Pulmonary Hypertension," Therapeatic Applications of Iloprost, A Volume in the Clinical Monograph Series, pp. 35–41, Apr. 1995.

S.C. Body, MD, et al.; "Nitric Oxide: Delivery, Measurement, and Clinical Application;" Journal of Cardiothoracic and Vascular Anesthesia, vol. 9, No. 6, Dec. 1995; pp. 748–763.

J.D. Young, et al.; "Delivery of Monitoring of Inhaled Nitric Oxide;" Intensive Care Med. Jan. 1996, vol. 22 pp. 77–86.

R. N. Channick, MD; "Pulsed Delivery of Inhaled Nitric Oxide to Patients with Primary Pulmonary Hypertension;" Chest, 1996; pp. 1545–1549.

S.M. Hudome, MD; "Precise Control of Nitric Oxide Concentration in the Inspired Gas of Continuous Flow Respiratory Devices;" Pediatric Pulmonology, vol. 22, No. 3, Sep. 1996; pp. 182–187.

Higenbottam, T.W., "Nitric Oxide And The Lung," Horizons in Medicine, No. 7, pp. 203–224 (1996).

Higenbottam, T., Waren, J., "Inhaled Nitric Oxide," The Lancet, vol. 348, No. 9039, pp. 1447–1448; Nov. 23, 1996.

Dupuy, P.M., Frostell, C.G., "Bronchial Effects Of Nitric Oxide," Nitric Oxide and the Lung, vol. 98, Chapter 15, pp. 285–311 (1997).

Gerlach, H., Falke, K.J., "Low Levels Of Inhaled Nitric Oxide In Acute Lung Injury," Nitric Oxide and the Lung, vol. 98, Chapter 14, pp. 271–283 (1997).

J. A. Leopold, et al.; "New Developments in Nitrosovasodilator Therapy;" Vascular Medicine, vol. 2, No. 3, 1997.

Katayama, Y., Higenbottam, T.W., Diaz de Atauri, M.J., Cremona, G., Akamine, S., Albert Barbera, J., Rodriguez–Roisin, R., "Inhaled Nitric Oxide And Arterial Oxygen Tension In Patients With Chronic Obstructive Pulmonary Disease And Severe Pulmonary Hypertension," Thorax, vol. 52, pp. 120–124 (1997).

H. Imanaka, MD, et al.; "Inaccuracies of Nitric Oxide Delivery Systems During Adult Mechanical Ventilation;" Anesthesiology, vol. 86, No. 3, Mar. 1997; pp. 676–688.

Marriott, H., Higenbottam, T., "The Role Of Nitric Oxide In Respiratory Disease," Schweiz Med Wochenschr, vol. 127, pp. 709–714, Apr. 26, 1997.

D. Hess, PhD, RRT, et al.; "Delivery Systems for Inhaled Nitric Oxide;" Respiratory Care Clinics of North America, vol. 3, No. 3, Sep. 1997; pp. 371–410.

Higenbottam, T., Marriott, H., Siddons, T., Smith, A.P.L., "Primary And Secondary Pulmonary Hypertension," Seminars in Respiratory and Critical Care Medicine, vol. 19, No. 1, pp. 91–95 (1998).

U. Klein, MD, et al.; "Nitric Oxide Delivery Systems;" Acta Anaesthesiologica Scandinavica, 1998; pp. 274–275 (4 pages total).

M. Francoe, et al.; "Inhaled Nitric Oxide: Technical Aspects of Administration and Monitoring;" Critical Care Medicine, vol. 26, No. 4, Apr. 1998; pp. 782–796.

D. D. Ivy, MD, et al.; "Acute Hemodynamic Effects of Pulsed Delivery of Low Flow Nasal Nitric Oxide in Children with Pulmonary Hypertension;" Journal of Pediatrics, vol. 133, No. 3, Sep. 1998; pp. 453–456.

M. J. Hiesmayr, et al.; "Performance of Proportional and Continuous Nitric Oxide Delivery Systems During Pressure– and Volume–Controlled Ventilation;" British Journal of Anaesthesia, vol. 81, No. 4, Oct. 1998; pp. 544–552.

Y. Katayama, MD, et al.; "Minimizing the Inhaled Dose of NO With Breath–By–Breath Delivery of Spikes of Concentrated Gas;" Journal of the American Heart Association—Circulation, vol. 98, No. 2, Dec. 1, 1998; pp. 2429–2432.

Higenbottam, T., Stenmark, K., Simonneau, G., "Treatments For Severe Pulmonary Hypertension," The Lancet, vol. 353, pp. 338–340, Jan. 30, 1999.

H. Schofnagl, et al.; "Proportional and Continuous NO Delivery Systems;" British Journal of Anaesthesia, vol. 2, No. 4, Apr. 1999; pp. 647–653.

Katayama, Y., Higenbottam, T.W., Cremona, G., Akamine, S., Demoncheaux, E.A.G., Smith, A.P.L., Siddons, T.E., "A Minimal Dose Of Inhaled Nitric Oxide Delivered As A 'Spike' Of Small Volume In Early Inhalation," Section of Respiratory Medicine, Division of Clinical Sciences, The Medical School, University of Sheffield.

* cited by examiner

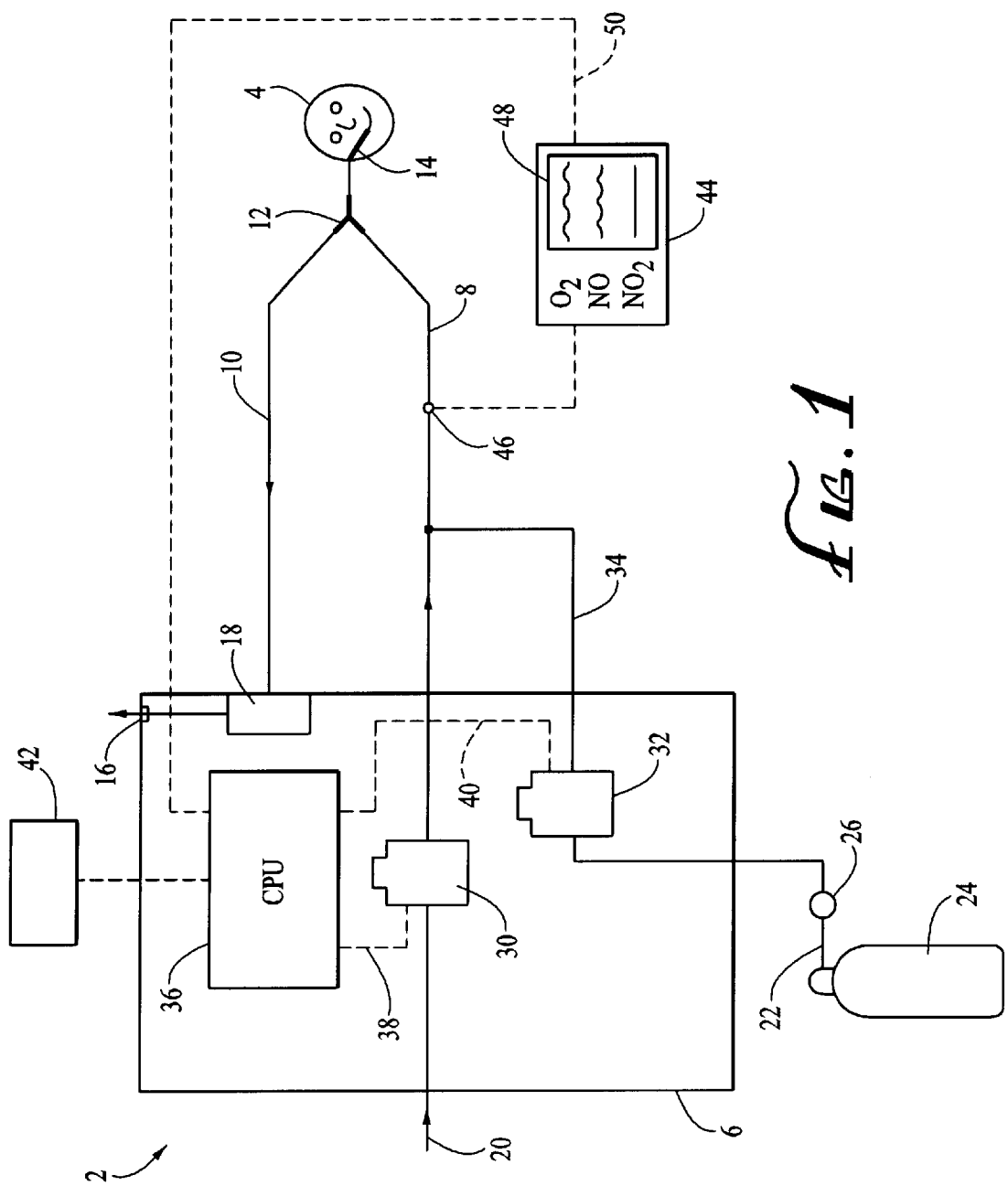

METHOD AND APPARATUS FOR DELIVERY OF INHALED NITRIC OXIDE TO SPONTANEOUS-BREATHING AND MECHANICALLY-VENTILATED PATIENTS

The invention generally relates to an apparatus and method for measurement, mixing, monitoring, and delivery of gases to a patient, including nitric oxide ("NO") and oxygen. More specifically, the invention relates to an apparatus and method of delivering gaseous NO to spontaneous-breathing patients as well as to patients connected to a mechanical ventilator.

NO is an environmental pollutant produced as a byproduct of combustion. At high concentrations (generally at or above 1000 ppm), NO is toxic. No also is a naturally occurring gas that is produced by the endothelium tissue of the respiratory system. In the 1980's, it wag discovered by researchers that the endothelium tissue of the human body produced NO, and that NO is an endogenous vasodilator, namely, an agent that widens the internal diameter of blood vessels.

With this discovery, numerous researchers have investigated the use of low concentrations of inhaled NO to treat various pulmonary diseases in human patients. See Higenbottam et al., Am. Rev. Resp. Dis. Suppl. 137:107, 1988. It was determined, for example, that PPH can be treated by inhalation of low concentrations of NO. With respect to pulmonary hypertension, inhaled NO has been found to decrease pulmonary artery pressure (PAP) as well as pulmonary vascular resistance (PVR).

Prior to the advent of NO inhalation therapy, pulmonary hypertension was treated by the administration of drugs known as systemic vasodilators. These drugs, such as prostacyclin, nitroprusside, hydroalazine, and calcium channel blockers suffered from the limitation that the drugs, by their nature, produced systemic effects. For example, the drugs not only decreased PAP levels, but also systemic blood pressure.

Unlike systemic vasodilators, inhaled NO acts as a selective pulmonary vasodilator, acting primarily on the endothelium tissue of the lung. Upon inhalation, NO is absorbed into the capillary blood in the precapillary airspaces and alveolar capillaries. Inhaled NO has negligible action beyond the site of its uptake since NO is rapidly inactivated by the reaction with hemoglobin to form methemoglobin.

The use of inhaled NO for PPH patients was quickly followed by the use of inhaled NO for other respiratory diseases. For example, NO has been investigated for the treatment of patients with increased airway resistance as a result of emphysema, chronic bronchitis, asthma, adult respiratory distress syndrome (ARDS), and chronic obstructive pulmonary disease, (COPD). Still other respiratory diseases where NO inhalation therapy is thought to be beneficial include, by way of illustration and not by way of limitation: allograft lung transplantation, ischemia-reperfusion injury, congestive heart failure, septic shock, and high-altitude pulmonary edema.

While NO has shown promising preliminary results with respect to the treatment and prevention of the diseases mentioned above, delivery methods and devices must cope with certain problems inherent with gaseous NO delivery. First, exposure to high concentrations-of NO is toxic. NO is toxic in high concentrations, especially over 1000 ppm. Even lower levels of NO can be harmful if the time exposure is relatively high. For example, the Occupational Safety and Health Administration (OSHA) has set exposure limits for NO in the workplace at 25 ppm time-weighted average for eight (8) hours. Typically, NO is administrated to patients in the concentration range of about 1 ppm to about 100 ppm.

Another problem with the delivery of NO is that NO rapidly oxidizes in the presence of oxygen to form $NO_2$, which is highly toxic, even at low levels. For example, OSHA has set exposure limits for $NO_2$ at 5 ppm. In any NO delivery device it is thus desirous to reduce, to the largest extent possible, the conversion of NO to $NO_2$. The rate of oxidation of NO to $NO_2$ is dependent on numerous factors, including the concentration of NO, the concentration of $O_2$, and the time available for reaction. One problem with the inhalation of NO is that when NO is therapeutically inhaled, it is often mixed with high concentrations of $O_2$. Consequently, this increases the conversion rate of NO to $NO_2$. It is thus preferable to minimize the contact time between NO and $O_2$ when the NO is combined with a source of oxygen gas.

Methods and devices for delivering NO to a patient have been developed to minimize the conversion of NO to $NO_2$. For example, with respect to the delivery of NO to patients connected to a mechanical ventilator, the $NO/NO_2$ stream has been introduced directly into the respiratory limb of a patient. See Martin Francoe, et al., *"Inhaled Nitric Oxide: Technical Aspects of Administration and Monitoring,"* Critical Care Medicine, Vol. 26, No. 4, pp. 785–87 April 1998. This arrangement has the advantage over other designs that combine and mix $NO/NO_2$ and $Air/O_2$ prior to their input to the ventilator since the contact time between NO and $O_2$ is reduced.

Another delivery method and device that reduces the exposure to $O_2$ and to a certain extent NO is disclosed in the U.S. Pat. No. 5,839,433 issued to Higenbottam. The '433 patent discloses a method and apparatus for supplying NO to a patient. According to the '433 patent, a very short pulse of NO is delivered intermittently, either at the start or end of inspiration. The '433 patent thus teaches the delivery of a bolus or plug of nitric oxide to the patient by administering a very short pulse of NO during inspiration. The timing of the delivery (beginning vs. late) is altered depending on the disease that is to be treated. When NO is desired in the lowermost depths of the lungs, for example, during treatment of pulmonary hypertension where NO acts on the small pulmonary arteries and capillaries, a short pulse is given at the beginning of inspiration. On the other hand, for asthma-like airway diseases, a very short pulse is administered near the end of inspiration. This method attempts to deliver NO to the desired location of the lungs. The method reduces the total exposure of the lungs to NO as well as reduces the total amount of NO available to react with $O_2$ to form toxic $NO_2$.

The pulses of NO delivered according to the '433 patent are of a predetermined width, which can be altered by changing the amount of time that a control valve is left open. The '433 patent, however, fails to disclose the proportional delivery of NO gas to the patient having a flow profile that tracks or is proportional or quasi-proportional to the flow profile of an oxygen-containing gas. Rather, the valve mechanism provides a bolus, or square wave-type "plug" of NO to the patient, the length of which, is altered by adjusting its width (i.e., holding the valve in the open position for a longer period of time). In this regard, the pulse has the flow profile of a square wave regardless of the profile of the patient's inspiration profile.

Generally, NO is administered to patients that are either spontaneously breathing or connected to a mechanical ventilator. In spontaneously breathing patients, a patient typically wears a tight fitting mask, transtracheal $O_2$ catheter, nasal cannula, or other tubing passing directly into the airway of a patient. NO is typically mixed with $O_2$ and air prior to introduction into the patient airway. See Dean Hess, Ph.D., et al., "*Delivery Systems for Inhaled Nitric Oxide*," Respiratory Care Clinics of North America, Vol. 3, No. 3, pp. 402–404 September 1997. These spontaneous systems, however, suffer from the limitation that the NO concentration can fluctuate within a relatively wide range. The dose of NO varies with the patient's ventilatory pattern due to the fact that the patient's inspiration profile changes on a breath-by-breath basis. The delivered dose of NO is thus approximated from assumptions regarding the patient's ventilatory pattern.

There are several different methods of delivering NO to a mechanically-ventilated patient. In one method, the $NO/N_2$ stream is premixed with $Air/O_2$ prior to entering the ventilator. While such pre-mixing may better permit the inspired concentration of NO to be controlled, the production of $NO_2$ is significantly higher given the longer contact time between NO and $O_2$. This is particularly true for ventilators with large internal volumes.

In another method of delivery, NO is continuously injected into the inspiratory limb of the ventilator circuit. This method, however, has difficulty maintaining a stable NO concentration throughout the entire inspiration flow. Moreover, when continuously injected NO is used with adult ventilators that have phasic flow patterns (flow only during inspiration), the inspiratory circuit fills with NO during expiration, and a large bolus of NO is delivered to the patient in the next breath. See, e.g., Dean Hess, Ph.D., et al., "*Delivery Systems for Inhaled Nitric Oxide*," Respiratory Care Clinics of North America, Vol. 3, No. 3, p. 381 September 1997. This method may result in an inspired NO concentration that may be more than double the calculated or estimated dose. In addition, the concentration of delivered NO varies with the length of the patient's expiration. For example, when the expiratory time is short, the delivered NO concentration is lower due to less time for filling the inspiratory limb with NO.

Yet another method of delivering NO involves intermittent injections of an NO-containing gas into the patient's inspiratory limb. In this regard, NO is delivered into the inspiratory limb only during the inspiratory phase. For this method to be acceptable, however, the flow from the ventilator must be continuously and precisely measured, and the injected does of NO must be precisely titrated such that the delivered NO and inspiratory flow waveform are not affected. See, Dean Hess, Ph.D., et al., "*Delivery Systems for Inhaled Nitric Oxide*," Respiratory Care Clinics of North America, Vol. 3, No. 3, p. 384, September 1997.

One such commercial device operating on the above-mentioned intermittent injection principle is the I-NOvent Delivery System (Ohmeda). In the I-NOvent Delivery System a device separate and apart from the mechanical ventilator injects NO directly into the inspiration circuit of the patient. Flow in the inspiration limb of the circuit is measured via a flow sensor and NO is injected in proportion to the measured flow to provide the desired dose. See, Dean Hess, Ph.D., et al., "*Delivery Systems for Inhaled Nitric Oxide*," Respiratory Care Clinics of North America, Vol. 3, No. 3, p. 395, September 1997.

Another commercial device utilizing intermittent injection of NO is the Nodomo device (Dragerwerk, Germany). The NOdomo device interfaces, like the I-NOvent Delivery System, with a separate mechanical ventilator. NO addition is controlled via a mass flow controller, adding a proportion of NO into the breathing circuit. Unlike the I-NOvent Delivery System, however, the NOdomo device controls NO flow delivery from an electronic flow controller that receives an input signal directly from the ventilator. See, Dean Hess, Ph.D., et al., "*Delivery Systems for Inhaled Nitric Oxide*," Respiratory Care Clinics of North America, Vol. 3, No. 3, p. 399 September 1997.

U.S. Pat. No. 5,558,083 issued to Bathe et al. discloses a NO delivery system. The delivery system can be used with a mechanical ventilator as well as a gas proportioning device for spontaneous-breathing. A CPU controls a proportional control valve that is in-line with a source of NO gas. The CPU calculates the desired flow from, among other things, the flow of breathing gas measured via a flow sensor 46 and NO concentration measured by NO sensor 65. The proportional control valve 24 is controlled to arrive at the desired NO concentration.

In a second embodiment of the Bathe et al. device, a supplemental supply of $O_2$ 74 is connected to the NO line. A proportional control valve 78 is positioned in-line with the $O_2$ supply 74 and reports to the CPU 56. As disclosed in the '083 patent, the $O_2$ is provided as a safety measure should the $O_2$ level fall below a critical level. Col. 8, lines 50–61. In the event that the level of $O_2$ has dropped below the minimum threshold, the CPU 56 directs the proportional flow controller to increase the flow of $O_2$ to the $NO/N_2$ stream.

The '083 patent, however, fails to teach or suggest the proportional-type control of $NO/N_2$, or $O_2$ to track or match the flow of either $O_2$ or the inspiration profile of a patient. Rather, the $O_2$ is used as a safety measure should the $O_2$ concentration fall below a threshold value. Moreover, in the devices disclosed in the '083 and '433 patents, residual NO gas is left in the device/inspiration limb between breaths.

It is thus desirous to have a device and method of delivery of NO to a patient that can control the delivery of an it NO-containing gas as well as an oxygen-containing gas to a patient via a single controller. The device preferably can provide either a constant concentration of NO to the patient during inspiration or a non-constant concentration of NO to the patient depending on the desired setting. In addition, the device preferably does not suffer from the limitation of other delivery systems, where NO may remain in the system between breaths. Namely, the device and method preferably eliminates any bolus or residue of NO-containing gas that might build-up between breaths.

SUMMARY OF THE INVENTION

In a first aspect of the invention a method of delivering a steady concentration of NO to a spontaneously breathing patient via delivery means is disclosed. The method includes the step of detecting the onset of inspiration by the patient. The inspiration flow profile is determined for an individual breath. An oxygen-containing gas is supplied to the delivery means, wherein the oxygen-containing gas has a flow profile that tracks the inspiration flow profile. A NO-containing gas is supplied to the delivery means, wherein the NO-containing gas has a flow profile that is proportionally less than the flow profile of the oxygen-containing gas throughout inspiration.

In a second, separate aspect of the invention, a method of delivering a non-constant concentration of nitric oxide to a spontaneously breathing patient via delivery means is disclosed. The method includes the steps of the first aspect, however, the NO-containing gas is supplied to the delivery means wherein the NO-containing gas has a flow profile that is less than, but closely tracks the oxygen-containing gas flow profile at the beginning of inspiration, and wherein the difference between the flow profile of the oxygen-containing gas and the flow profile of the nitric oxide-containing gas progressively increases through the remainder of inspiration.

In a third, separate aspect of the invention, another method of delivering a non-constant concentration of nitric oxide to a spontaneously breathing patient via delivery means is disclosed. The method includes the steps of the first aspect, however, the nitric oxide-containing gas has a flow profile that is substantially less than the oxygen-containing gas flow profile at the beginning of inspiration compared to the end of inspiration, and wherein the difference between the flow profile of the oxygen-containing gas and the flow profile of the nitric oxide-containing gas progressively decreases throughout the remainder of inspiration.

In another aspect of the invention, different embodiments of a delivery device are disclosed for practicing it the various methods for the delivery of NO to a spontaneously breathing patient.

In yet another aspect of the invention, a method of delivering a constant concentration of nitric oxide to a mechanically-ventilated patient via single controller is disclosed. In the method, the desired inspiration flow profile is set in the controller. The flow rate of an oxygen-containing gas is varied in accordance with the inspiration flow profile by delivering a first signal from said controller to a first control valve controlling the rate of flow of an oxygen-containing gas to the patient, thereby creating a flow profile of oxygen-containing gas. The flow rate of a nitric oxide-containing gas is varied in accordance with the inspiration profile by delivering a second signal from said controller to a second control valve controlling the rate of flow of the nitric oxide-containing gas to the patient, creating a flow profile of nitric oxide-containing gas. The nitric oxide-containing flow profile is less than and proportional to the flow profile of the oxygen-containing gas throughout patient inspiration.

In still another aspect of the invention, a method of delivering a non-constant concentration of NO to a mechanically-ventilated patient is disclosed. The method includes the steps of the previously recited method, however, the flow rate of the nitric oxide-containing gas is varied to create a flow profile of nitric oxide-containing gas that is less than, but closely tracks the oxygen-containing gas flow profile in the beginning of the inspiration, wherein the difference between the flow profiles of the oxygen-containing gas and the nitric oxide-containing gas progressively increases through the remainder of inspiration.

In yet another method for delivering a non-constant concentration of NO to a mechanically-ventilated patient, the flow rate of the nitric oxide-containing gas has a flow profile that is substantially less than the oxygen-containing gas flow profile at the beginning of inspiration, and wherein the difference between the flow profile of the oxygen-containing gas and the nitric oxide-containing gas progressively decreases throughout the remainder of inspiration.

In another aspect of the invention, different embodiments of a delivery device are disclosed for practicing the mechanical ventilation methods set-forth above.

In another aspect of the invention, a method of delivering nitric oxide via delivery means to a mechanically or spontaneously breathing patient having a certain inspiration profile is disclosed. The method includes the aspect of an air flush to eliminate remaining nitric oxide or enriched oxygen. The method includes the step of supplying in a first breath a mixture of oxygen-containing gas and a nitric oxide-containing gas to the delivery means, the oxygen-containing gas and a nitric oxide-containing gas.having a flow profile proportional or quasi proportional to the inspiration flow profile. In at least one next breath, a source of enriched oxygen-containing gas is supplied having a flow profile that is proportional or quasi-proportional to the inspiration flow profile. A source of air is supplied at or near the end of the first and next breaths to flush the delivery means of enriched oxygen and nitric oxide.

In another aspect of the invention, a method of delivering nitric oxide to a spontaneously breathing patient via delivery means is disclosed. The method includes the step of detecting the onset of inspiration. An oxygen-containing gas is supplied to the delivery means, wherein the oxygen-containing gas has a pre-programmed flow profile. A nitric oxide-containing gas is supplied to the delivery means, wherein the nitric oxide-containing gas has a pre-programmed flow profile that is proportional or quasi-proportional to the flow profile of the oxygen-containing gas throughout inspiration.

In still another aspect of the invention, a device for delivering nitric oxide to a spontaneous-breathing patient is disclosed. The device includes a source of an oxygen-containing gas connected via tubing to a patient inspiration interface device. A source of a nitric oxide-containing gas is connected via tubing to the patient inspiration interface device. A first proportional flow controller is located between the source of oxygen-containing gas and the patient inspiration interface device for varying the flow rate of the oxygen-containing gas to the patient inspiration interface device. A second proportional flow controller is located between the source of nitric oxide-containing gas and the patient inspiration interface device for varying the flow rate of the nitric oxide-containing gas to the patient inspiration interface device. An inspiration flow profile sensor is provided for detecting the onset of inspiration of the patient. The device includes a controller for controlling the first and second proportional flow controllers in response to the detection of the onset of inspiration from the inspiration flow profile sensor, the first and second proportional flow controllers being controlled such that the nitric oxide-containing gas has pre-programmed flow profile that is proportional or quasi-proportional to the flow profile of the oxygen-containing gas throughout inspiration.

BRIEF DESCRIPTION OF THE DRAWINGS

FIG. 1 is a schematic illustration of the device being used with a patient supported by mechanical ventilation.

Figure 2A:
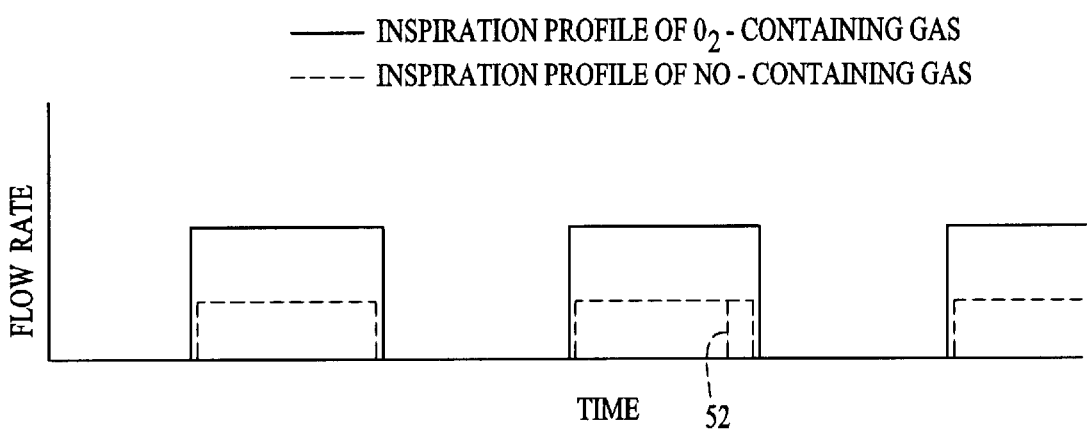
FIG. 2(a) illustrates a square-shaped inspiration profile of the oxygen-containing gas and the NO-containing gas for delivering a constant concentration of NO to a patient.

DETAILED DESCRIPTION OF THE PREFERRED EMBODIMENT.

Referring now to the Figures, FIG. 1 shows a schematic representation of the device 2 for delivering NO gas to a patient 4 connected to a mechanical ventilator 6. In this embodiment of the invention, the device 2 is the mechanical ventilator 6 since both control of patient inspiration, expiration, and delivery of NO are all controlled by the device 2. In this regard, a separate NO administration device is not needed since the device 2/mechanical ventilator 6 delivers to NO gas to the patient 4.

As seen in FIG. 1, the device 2 includes an inspiration limb 8 and an expiration limb 10. The inspiration limb 8 and the expiration limb 10 are connected via a Y-piece 12. The Y-piece 12 connects to delivery means for delivering the gaseous mixture to the patient 4. The delivery means preferably includes a patient inspiration interface device 14. The patient inspiration interface device 14 can be any number of devices that connect a generally hollow, tubular construction (i.e., flexible tubing) to the respiratory tract of the patient 4. For example, by way of illustration and not by limitation, the patient inspiration interface device 14 can include a tube for intubation into the patient's 4 airway, a nasal cannula, a face mask, or a transtracheal catheter. Flexible, hollow tubing is typically used in the inspiration limb 8 and expiration limb 10. The expiration limb 10 returns to the device 2 where the expired gases pass through an exhaust port 16. The expired gas can be vented to directly to the atmosphere, or alternatively, the expired gas can pass through an optional gas scavenger system 18 to remove NO and $NO_2$ from the expiration gas prior to atmospheric venting.

The inspiration limb 8 is attached to the other end of the Y-piece 12 and serves as a transport medium for the sources of oxygen-containing gas 20 and NO-containing gas 22 to the patient 4. The source of oxygen-containing gas 20 can come from any number of sources, including, for example, atmospheric air, compressed air, compressed air enriched with oxygen, and a mixture of oxygen and $N_2$. The main requirement for the oxygen-containing gas 20 is that the gas contain at least some component of oxygen. Typically, when the device 2 is connected to a patient 4, the oxygen-containing gas 20 is delivered to the device via a dedicated line in a medical facility having a pre-set oxygen concentration. Alternatively, the oxygen-containing gas 20 can be delivered via a pressurized cylinder.

The source of NO-containing gas 22 is shown in FIG. 1 as being a pressurized cylinder 24 containing NO gas. While the use of a pressurized cylinder 24 is the preferable method of storing the NO-containing gas 22, other storage and delivery means, such as a dedicated feed line (wall supply), can also be used. Typically, the NO-containing gas 22 is a mixture of $N_2$ and NO. While $N_2$ is typically used to dilute the concentration of NO, any inert gas can also be used. When the NO-containing gas 22 is stored in pressurized cylinder 24, it is preferable that the concentration of NO in the pressurized cylinder 24 fall within the range of about 800 ppm to about 1200 ppm. Commercial nitric oxide manufacturers typically produce nitric oxide mixtures for medical use at around the 1000 ppm range. Extremely high concentrations of NO are undesirable because accidental leakage of NO gas is more hazardous, and high partial pressures of NO tends to cause the spontaneous degradation of NO into nitrogen.

While the inspiration concentration of NO gas generally falls within the range of about 1 ppm to about 100 ppm, it is preferable to use a source of NO-containing gas 22 at a higher concentration for several reasons. First, it is generally not possible to special-order or purchase pressurized cylinders 24 containing NO at a requested concentration. While it is possible to create pressurized cylinders 24 with lower concentrations of NO by mixing with an additional volume of inert gas, this process is time consuming, adds additional cost, and has the potential of introducing oxygen into the gas mixture. U.S. Pat. No. 5,839,433 issued to Higenbottam, for example, utilizes a low concentration source of NO. (100 ppm NO cylinder). Pressurized cylinders 24 with low concentrations of NO are also not as desirable from an economic standpoint. Since a smaller quantity of NO is contained within pressured cylinders 24 having low NO concentrations (i.e., 100 ppm), these pressurized cylinders 24 exhaust their supply of NO much more quickly than a pressurized cylinder 24 containing a higher concentration of NO. Consequently, low NO ppm pressurized cylinders 24 are changed more frequently than pressurized cylinders 24 having a larger concentration of NO. This increases the overall cost of the NO treatment.

Since the pressure in the pressurized cylinder 24 is relatively high compared to the pressure of the breathing gas, a pressure regulator 26 is preferably employed to reduce the pressure of the NO-containing gas 22 prior to introduction to the ventilator 4.

The device 2 further includes a first control valve 30 that is located in-line between the oxygen-containing gas 20 and the inspiration limb 8. The first control valve 30 thus receives the oxygen-containing gas 20 at an input port and modulates, or controls the flow of the oxygen-containing gas 20 into the inspiration limb 8 through a second export port. The first control valve 30 can include, for example, a proportional control valve that opens (or closes) in a progressively increasing (or decreasing if closing) manner depending on an electronic input. As another example, the first control valve 30 can also include a mass flow controller. The first control valve 30 can include any number of control valves that can quickly and accurately alter the flow rate of a gas across a relatively wide range of flow rates.

The output of the first control valve 30 leads to the inspiration limb 8 of the patient 4. In this regard, the first control valve 30 controls the inspiration profile of the oxygen-containing gas 20. The inspiration profile of the oxygen-containing gas 20 is the flow rate of the oxygen-containing gas 20 as a function of inspiration time. The inspiration profile of the oxygen-containing gas 20 can be seen in FIG. 2(a).

Still referring to FIG. 1, a second control valve 32 is located in-line between the NO-containing gas 22 and the inspiration limb 8. The second control valve 32 thus receives the NO-containing gas 22 at an input port and modulates, or controls the flow of the NO-containing gas 22 into the inspiration limb 8 through a second export port. The second control valve 32 can include, for example, a proportional control valve that opens (or closes) in a progressively increasing (or decreasing if closing) manner depending on an electronic input. As another example, the second control valve 32 can also include a mass flow controller. The second control valve 32 can include any number of control valves that can quickly and accurately alter the flow rate of a gas across a relatively wide range of flow rates. Like the first control valve 30, the inspiration profile of the second control valve 32 controls the inspiration profile of the NO-containing gas 22. The inspiration profile of the NO-containing gas 22 is the flow rate of the NO-containing gas 22 as a function of time.

Exiting the second control valve 32 is a NO-addition line 34 that enters the inspiration limb 8. The NO-addition line 34 thus carries the controlled flow of NO-containing gas 22 to the inspiration limb 8. Preferably, the NO-addition line 34 can enter the inspiration limb 8 at any point between the ventilator 6 and the patient inspiration interface device 14. Most preferably, the NO-addition line 34 enters the inspiration limb 8 at a location that is prior to the Y-piece 12. When an optional gas monitor 44, described more fully below, is included as part of the device 2 to measure the concentration of inspired gases in the inspiration limb 8, the NO-addition line 34 preferably enters the inspiration limb 8 upstream of the location where the gas concentration measurements are made. Even more preferably, the NO-addition line 34 enters the inspiration limb 8 upstream of where the gas concentration measurements are made at a distance that is equal to, or greater than, six-times the internal diameter of the tubing used in the inspiration limb 8.

The device further includes CPU 36. The CPU 36 acts as a controller of the first and second control valves 30, 32. The CPU 36 sends, via signal lines 38, 40, signals to control the opening and closing of the control valves 30, 32. As one option, the CPU 36 contains preset instructions on controlling the inspiration profiles of the oxygen-containing gas 20 and the NO-containing gas 22. The instructions can be stored in read-only-memory (ROM) on the CPU 36, or alternatively, the instructions can be input to the CPU 36 via an input device 42. The input device 42 can be any number of devices that encode the flow profiles of the oxygen-containing gas 20 and the NO-containing gas 22. These include, by way of illustration, and not by way of limitation: a computer, a diskette, a control panel, and the like.

The input device 42 can input, for example, the set-point concentration of NO in the breathing gas. The desired set-point concentration of NO is typically set by a physician, for example. The input device 42 can thus alter the degree of proportionality between the flow profile of the oxygen-containing gas-20 and the flow profile of the NO-containing gas 22. A higher degree of proportionality (i.e., the flow profile of the NO-containing gas 22 more closely tracks the flow profile of the oxygen-containing gas 20) would generally produce a higher concentration of inspired NO. The degree of proportionality also affects the timing of the NO gas purge.

The input device 42 may also input gas purge parameters to the CPU 36 to determine when the flow profile of the NO-containing gas 22 is truncated. This can be done, for example, by establishing a time after inspiration is started at which the flow profile of the NO-containing gas 22 is dropped to zero. Alternatively, the NO-containing gas 22 can terminate once the flow rate of the oxygen-containing gas 20 drops below a certain pre-set level. These settings can be input to the CPU 36 via the input device 42.

By modulating the flow rates of both the oxygen-containing gas 20 and the NO-containing gas 22, the CPU 36 controls the inspiration flow profile of each breath of the patient. The CPU 36 can create any number of inspiration flow profiles. For example, the CPU 36 can deliver a sine-shaped, square-shaped, or ramp-shaped inspiration flow profile. Of course, other inspiration flow profiles other than those specifically mentioned-above can also be delivered to the patient 4. The CPU 36 can also control other parameters such as the respiratory rate, tidal volume, and inspiration pressure settings. These parameters can be sent to the CPU 36 via input device 42.

The present invention contemplates using a CPU 36 that gives the device 2 complete programmability. In this regard, the flow profiles of the both the oxygen-containing gas 20 and the NO-containing gas 22 can be controlled during a single breath. While proportional and quasi-proportional flow profiles are disclosed in greater detail herein, it should be appreciated that any flow profile (of the oxygen-containing gas 20 or the NO-containing gas 22) can be produced for a single breath of a patient 4. Complete programmability is also possible where the device employs input device 42.

While CPU 36 is shown as the preferred controller for controlling the flow profiles of the oxygen-containing gas 20 and the NO-containing gas 22, the present invention further contemplates using an analog switching mechanism (not shown) as an alternative controller.

Figure 2B:
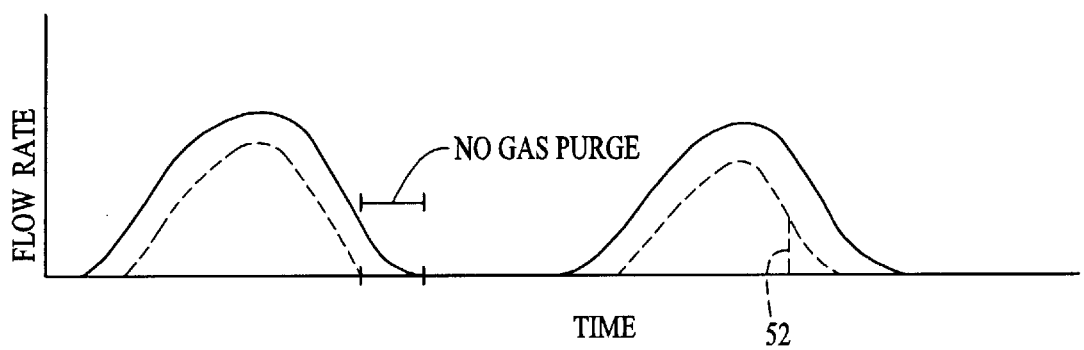
FIG. 2(b) illustrates a sine-shaped inspiration profile of the oxygen-containing gas and the NO-containing gas for delivering a constant concentration of NO to a patient.

A description of the method of operation of the device 2 will now be given. In the standard continuous mandatory ventilation mode, the device 2 delivers to a patient 4 a preset tidal volume at a predetermined respiratory rate. The inspiration flow profile that is desired (e.g., sine, square, or ramp) is delivered to the patient 4 by administering an oxygen-containing gas 20 and an NO-containing gas 22 that have flow profiles that are similar to the inspiration flow profile that is desired. FIGS. 2(a)–2(b) show the flow profiles of the oxygen-containing and NO-containing gases 20, 22. As can best be seen in FIG. 2(a), the flow profile of the NO-containing gas 22 is proportional to the flow profile of the oxygen-containing gas 20. Proportional is meant to indicate that the flow rate of the NO-containing gas 22 is less than, but proportionally tracks the flow profile of the oxygen-containing gas 20 throughout the patient's inspiration (the exception to this being the optional truncation of NO flow as described more fully below). In this regard, the delivered gas mixture of NO and oxygen has near constant concentration. The patient 4 thus receives a steady concentration of NO throughout inspiration.

The proportional flow is accomplished via the single CPU 36. The CPU 36 sends signals to the first and second controller valves 30, 32 to keep the flow of the NO-containing gas 22 lower, but in proportion to the flow of the oxygen-containing gas 20. Since a single CPU 36 is used to control both the first and second control valves 30, 32, there is no need to measure and report back to a control unit, the flow rate of either the NO-containing gas stream 22 or the oxygen-containing gas stream 20 via a flow sensor or the like.

Figure 2C:
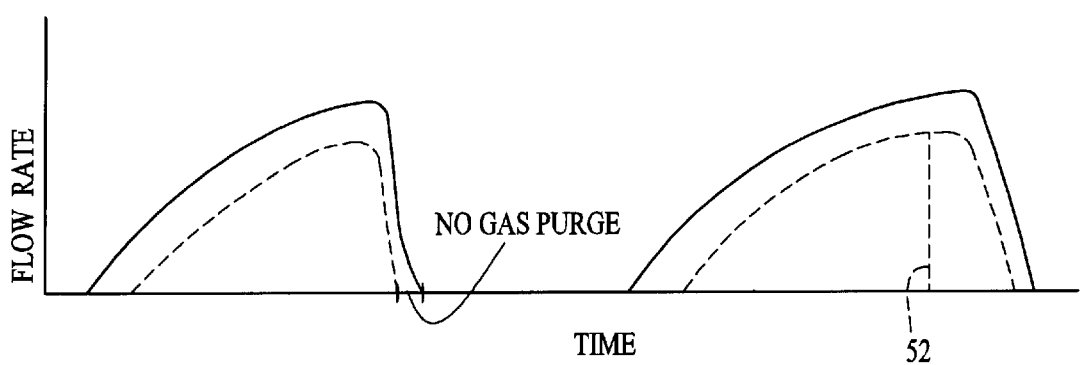
FIG. 2(c) illustrates a ramp-shaped inspiration it profile of the oxygen-containing gas and the NO-containing gas for delivering a constant concentration of NO to a patient.

The proportional flow control also has the benefit of purging the inspiration limb 8 of NO-containing gas 22 during certain inspiration flow patterns. For example, as seen in FIGS. 2(b) & 2(c), the flow rate of the NO-containing gas 22 reaches zero near the end portion of inspiration while the oxygen-containing gas 20 continues to have positive flow. In this regard, the flow of oxygen-containing gas 20 purges the inspiration limb 8 of NO until the next breath.

Alternatively, the CPU 36 can send a close-valve signal to the second control valve 32 near the end of patient inspiration. This close-valve signal truncates the flow profile (the truncated flow profile 52 is shown in FIGS. 2(a)–(c)) of the NO-containing gas 22 and leaves the oxygen-containing gas 20 as the only flow. The oxygen-containing gas 20 thus purges the inspiration limb 8 of NO.

Figure 3A:
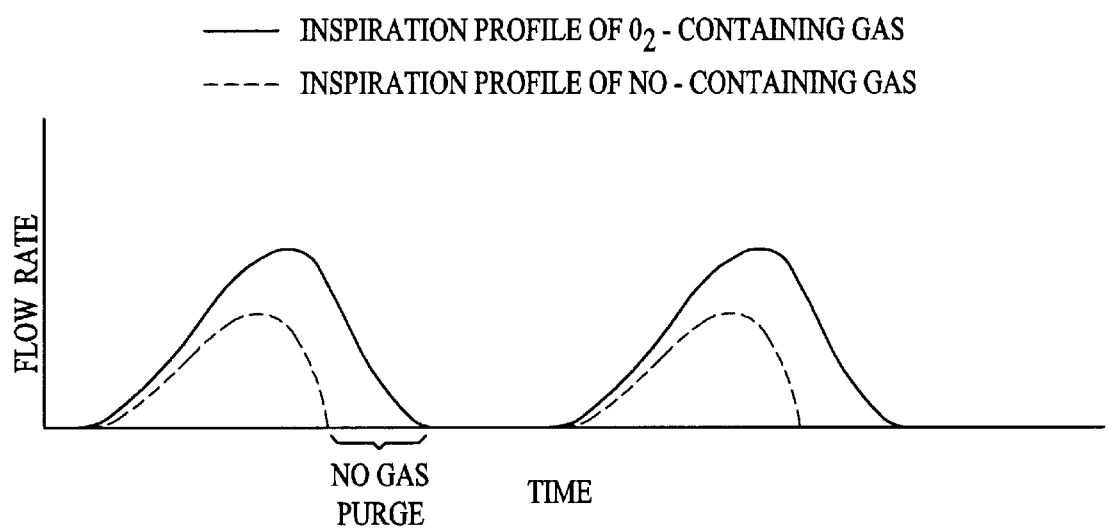
FIG. 3(a) illustrates the inspiration profile of the oxygen-containing gas and the NO-containing gas for delivering a non-constant concentration of NO to a patient, wherein the concentration of NO is higher at the beginning of inspiration than at the end of inspiration.
Figure 3B:
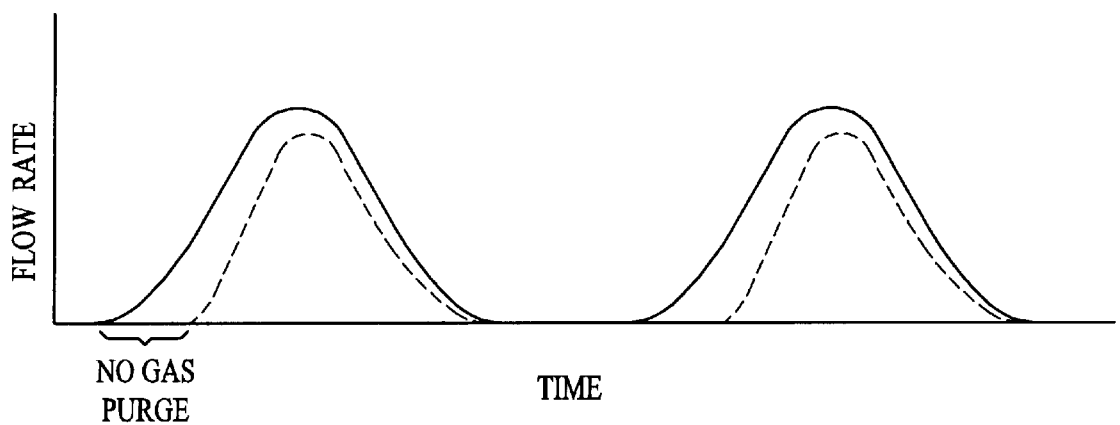
FIG. 3(b) illustrates the inspiration profiles of the oxygen-containing gas and the NO-containing gas for delivering a non-constant concentration of NO to a patient, wherein the concentration of NO is higher at the end of inspiration than at the beginning of inspiration.

As an alternative embodiment, the CPU 36 controls the flow of the NO-containing gas 22 and the oxygen-containing gas 20 to provide for a non-constant concentration of NO in the breathing gas of a patient 4. FIGS. 3(a) & 3(b) show the flow profiles of the operation of the device 2 according to this embodiment.

FIG. 3(a) shows a variable concentration delivery mode for NO that provides a higher concentration of NO to the patient 4 during the beginning of inspiration. As seen in FIG. 3(a), the flow profile of the NO-containing gas 22 is less than the flow profile of the oxygen-containing gas 20. In addition, the flow profile of the NO-containing gas 22 closely tracks the oxygen-containing gas 20 flow profile at the beginning of inspiration (quasi-proportional), but begins to tail-off as inspiration progresses. In this manner, the difference between the flow profiles of the oxygen-containing gas 20 and the NO-containing gas 22 progressively increases through the remainder of inspiration. In this method of delivery, a higher concentration of NO is delivered to the patient 4 at the beginning of inspiration than at the end of inspiration. This flow profile is used when it is desirous for NO to be delivered deep within the lungs, for instance, to treat pulmonary hypertension. Unlike the NO delivery method of the '433 patent that delivers a discrete bolus or short plug of NO, the present method provides a gradual gradient of NO in the lungs wherein the concentration of NO in the upper airway is lower than the concentration of NO in the lowermost regions of the lung. In addition, the flow profile of the NO-containing gas 22 more closely matches the flow profile of the oxygen-containing gas 20. The flow profile of the NO-containing gas 22 is not a square wave as disclosed in the '433 patent. Rather, the flow profile is quasi-proportional to the oxygen-containing gas 20 profile.

This method is advantageous over the method of delivery disclosed in the '433 patent because the bolus delivered in the '433 patent is of such a short length that the targeted area of the lung can be missed entirely. By having a continuous tapering of NO concentration, it is assured that the target area of the lungs is bathed in at least some concentration of NO. Moreover, since the difference between the flow rate of the oxygen-containing gas 20 and the NO-containing gas 22 increases (or decreases as shown in FIG. 3(b)) during the time of inspiration, the total amount of NO delivered per breath is smaller when compared to a square wave profile of NO. The pressurized cylinder 24 containing the NO-containing gas 22 thus needs less frequent changing. Another important aspect of this method of delivery is that the flow profile of the NO-containing gas 22 reaches zero prior to the flow profile of the oxygen-containing gas 20. See FIGS. 3(a) and 3(b). The oxygen-containing gas 20 that continues to flow aids in purging the inspiration limb 8 of NO.

With respect to the flow profile shown in FIG. 3(a), and as stated previously, the difference between the flow profiles of the oxygen-containing gas 20 and the NO-containing gas 22 progressively increases through the remainder of inspiration. The rate of this increase, however, may be controlled by the CPU 36. For example, the increase may be linear, non-linear, exponential, etc., depending on the desired flow profile of the NO-containing gas 22. Further, the rate of this increase may be set by the input device 42.

Referring now to FIG. 3(b), another flow profile is shown for the NO-containing gas 22 that provides for a greater NO concentration at the end of the patient's 4 inspiration profile.

As seen in FIG. 3(b), the flow profile of the NO-containing gas 22 is less than the flow profile of the oxygen-containing gas 20. In addition, the flow profile of the NO-containing gas 22 is substantially less than the oxygen-containing gas 20 at the beginning of inspiration. Preferably, the flow rate of the NO-containing gas 22 is zero at the beginning of inspiration, while the flow rate of the oxygen-containing gas 20 is positive. In addition, as inspiration proceeds, the difference between the flow profile of the oxygen-containing gas 20 and the NO-containing gas 22 progressively decreases. In this profile, a higher concentration of NO is delivered to the upper airway region of the lungs. This method is used, for example, in breathing diseases relating to broncho-constriction of the airways, such as asthma.

With respect to the flow profile shown in FIG. 3(b), the difference between the flow profiles of the oxygen-containing gas 20 and the NO-containing gas 22 progressively decreases through the remainder of inspiration. The rate of this decrease, however, may be controlled by the CPU 36. For example, the decrease may be linear, non-linear, exponential, etc., depending on the desired flow profile of the NO-containing gas 22. Further, the rate of this decrease may be set by the input device 42.

With respect to the purge feature of this method, at the beginning of the inspiration profile, the oxygen-containing gas 20 is flowing, but the NO-containing gas 22 is not. Consequently, the flow of the oxygen-containing gas 20 acts to purge the inspiration limb 8 of NO that may have remained from the previous breath.

Figure 4A:
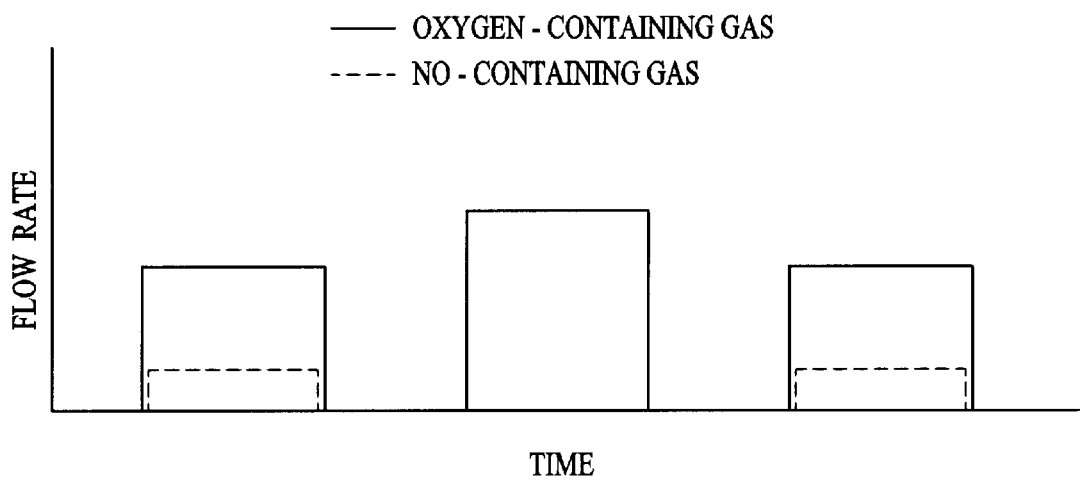
FIG. 4(a) is a flow profile of oxygen-containing gas and NO-containing gas where enriched-oxygen is delivered between breaths.

In another flow profile, shown in FIG. 4(a), a patient 4 receives a first inhalation containing both oxygen-containing gas 20 and NO-containing gas 22. In the next inhalation breath, the patient receives just oxygen-containing gas 20. Preferably, this inspiration contains a relatively high concentration of oxygen-containing gas 20 (oxygen-enriched). In the third inspiration, the patient 4 again receives an oxygen-containing gas 20 and an NO-containing gas 22. While the flow profile shown in FIG. 4(a) is shown as alternating between oxygen-containing gas-only 20 and NO-containing gas 22 plus oxygen-containing gas 20, the profile could also include, for example, two or more oxygen-containing gas 22-only inspirations between inspirations having both oxygen-containing gas 20 and NO-containing gas 22.

Figure 4B:
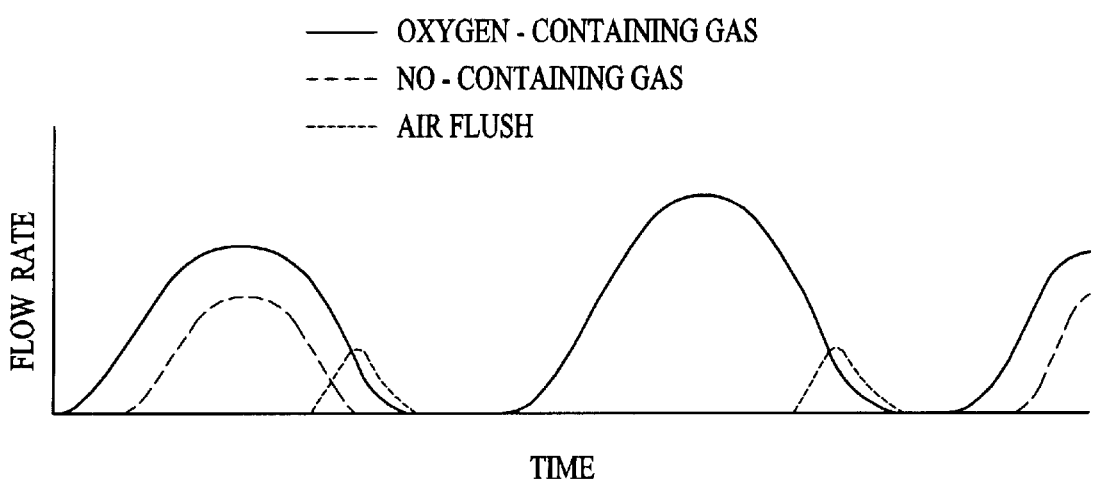
FIG. 4(b) shows the flow profile of the oxygen-containing gas, the No-containing gas, and the air flush according to one aspect of the invention.

Yet another flow profile is shown in FIG. 4(b). In FIG. 4(b), a patient 4 is delivered, on inspiration, a flow profile including an oxygen-containing gas 20 and a NO-containing gas 22. At or near the end of this inspiration, an air flush is delivered to the patient 4. The air flush serves to remove any NO-containing gas 22 that may be in the inspiration limb 8.

In the next inspiration, an oxygen-containing gas 20 is delivered to the patient 4 without any NO-containing gas 22. Preferably, the oxygen-containing gas 20 includes an elevated level of oxygen (enriched-oxygen). At or near the end of this inhalation, another air flush is delivered to the patient 4. This air flush is delivered to the patient 4 and serves to remove any enriched-oxygen remaining in the inspiration limb 8 as well as any residual NO gas.

Figure 5:
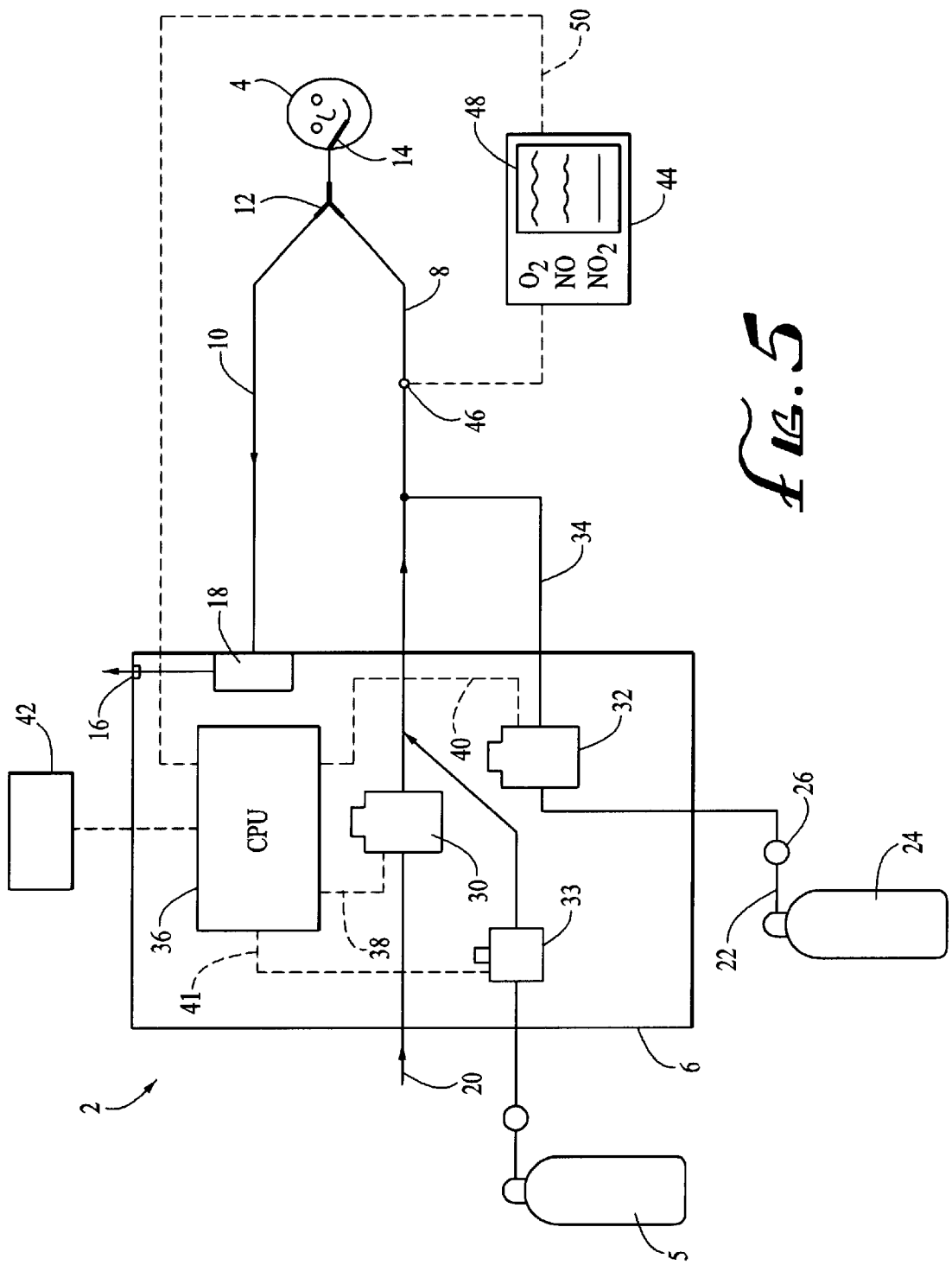
FIG. 5 is a schematic illustration of a device being used with a patient supported by mechanical ventilation wherein the air flush aspect is utilized.

In this embodiment, there are two separate sources of oxygen-containing gas 20. One source is the air used to flush the inspiration limb 8 while the other source is the enriched-oxygen-containing gas 20. The source of air for the air flush can be, for example, a separate pressurized cylinder, wall supply, compressor, pump, or the like. FIG. 5, for example, shows the air being stored in a pressurized cylinder 25 while the enriched oxygen-containing gas 20 enters the device via a wall supply or the like. The flow of air is modulated by a third control valve 33 that is controlled by the CPU 36 via signal line 41.

It should be noted that by controlling the flow rates of the oxygen-containing gas 20 and the NO-containing gas 22 via a single CPU 36, the device 2 can use a pressurized cylinder 24 having a relatively high concentration of NO (about 1000 ppm), since the second flow controller 32 is always controlled to provide a smaller flow rate of NO-containing gas 22 than the flow rate of the oxygen-containing gas 20.

The device 2 can further include an optional gas monitor 44. The gas monitor 44 preferably monitors the concentration of one or more of the following gases in the inspiration limb 8 of the device 2: oxygen, NO, and $NO_2$. The gas monitor 44 determines the concentration of gas(es) via a sensor(s) 46 located in the inspiration limb 8. The sensor(s) 46 can be a chemilluminesence-type, electrochemical cell-type, or spectrophotometric-type sensor 46 based on the accuracy and response time desired. The gas monitor 44 preferably includes a display screen 48 that illustrates, on a real-time basis or as close to a real-time basis as possible, the concentrations of the measured gases. The gas monitor 44 preferably reports the gas concentration data to the CPU 36 via signal line 50.

As an optional safety feature of the device 2, the CPU 36 can use the real-time concentration data to determine if the NO or $NO_2$ concentration levels exceed certain predetermined set-points input via input device 42. For example, if the $NO_2$ concentration exceeds the set-point concentration, the CPU can send a close-valve signal to the second control valve 32. In this regard, the NO-containing gas 22 is shut-off entirely.

In addition, the level of oxygen in the gas stream can also be monitored via the monitor 44. If the oxygen concentration drops below a certain concentration, the CPU 36 can decrease the flow of the NO-containing gas 22 and/or increase the flow rate of the oxygen-containing gas 20.

It should be noted that the above-described device 2 can also be used in modes other than continuous mandatory ventilation. For example, the device 2 can also be used with assisted ventilation, synchronized intermittent ventilation (SIMV), intermittent mandatory ventilation (IMV), and pressure support ventilation. Still other modes of operation will also work with the device 2.

Figure 6:
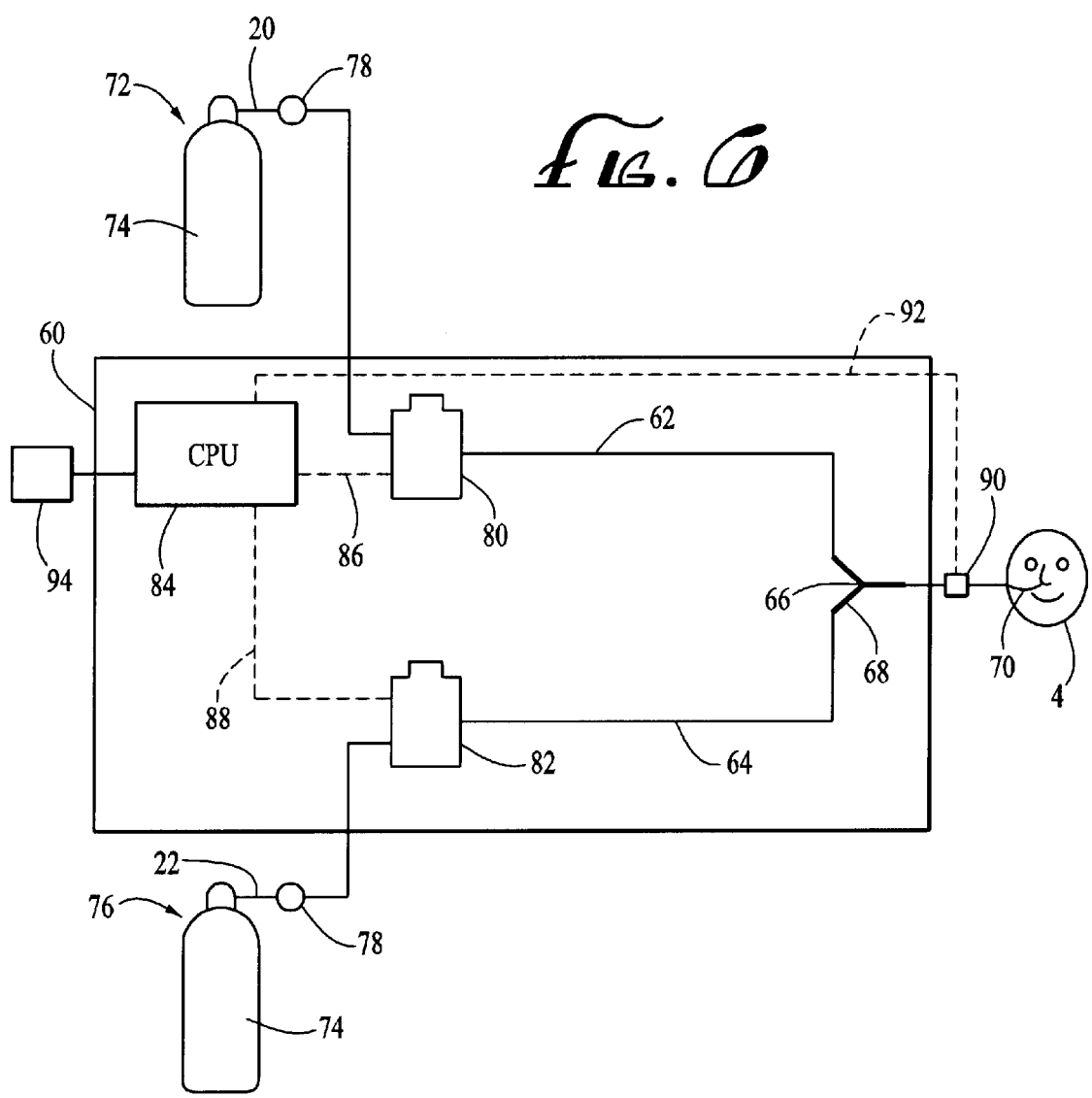
FIG. 6 is a schematic illustration of the device being used with a spontaneously breathing patient.

In another separate aspect of the invention, as shown in FIG. 6, a device 60 for a spontaneously breathing patient 4 is disclosed. The device 60 includes an oxygen-containing gas limb 62 and a NO-containing gas limb 64. Both the oxygen-containing gas limb 62 and a NO-containing gas limb 64 are preferably made of a hollow, flexible tubing material. The oxygen and NO limbs 62, 64 combine at a mixing point 66. The mixing point 66 may include a Y-piece 68 that connects with another hollow flexible tube that then travels to the patient 4. The combined gases enter the patient's airway via delivery means. The delivery means preferably includes a patient inspiration interface device 70. By way of illustration and not by way of limitation, the patient inspiration interface device 70 can include a tube for intubation into the patient's 4 airway, a nasal cannula, a face mask, or transtracheal catheter.

A source 72 of oxygen-containing gas 20 delivers the oxygen-containing gas 20 into the oxygen-containing gas limb 62. The source 72 of oxygen-containing gas 20 preferably is a pressurized cylinder 74. The pressurized cylinder 74 can contain atmospheric air, compressed air, compressed air mixed with oxygen, or a mixture of oxygen and nitrogen. The main requirement for the oxygen source 72 is that the gas contain at least some component of oxygen.

While the pressurized cylinder 74 is the preferable method of storing the oxygen source 72, other storage means such as a dedicated feed line (wall supply), can also be used. Alternatively, the oxygen can be delivered from a compressor or pump.

The NO source 76 is shown as a pressurized cylinder 74. While the use of a pressurized cylinder 74 is the preferable method of storing the NO-containing gas 22, other storage and delivery means, such as a dedicated feed line, can also be used. Preferably, the NO-containing gas 22 is a mixture of $N_2$ and NO. While $N_2$ is typically used to dilute the concentration of NO, any inert gas can also be used. When the NO-containing gas 22 is stored in pressurized cylinder 74, it is preferable that the concentration of NO in the cylinder fall within the range of about 800 ppm to about 1200 ppm.

As with the inspiration concentration of NO gas in the mechanical ventilator embodiment, it is generally preferable that the NO concentration fall with the range of about 1 ppm to about 100 ppm. In the spontaneous-breathing embodiment, it is preferable to use a NO source 76 at higher concentrations for the same stated reasons for the mechanical ventilator embodiment.

When pressurized cylinders 74 are used to store the oxygen and NO-containing gases 20, 22, pressure regulators 78 are preferably used to reduce the pressures of the respective gases.

The device 60 includes a first control valve 80 that is located in-line between the source 72 of oxygen-containing gas 20 and the oxygen-containing gas limb 62. As with the mechanical ventilator device 2, The first control valve 80 thus receives the oxygen-containing gas 20 at an input port and modulates, or controls the flow of the oxygen-containing gas 20 into the oxygen-containing gas limb 62 through a second export port. The first control valve 80 can include, for example, a proportional control valve that opens (or closes) in a progressively increasing (or decreasing if closing) manner depending on an electronic input. As another example, the first control valve 80 can also include a mass flow controller. The first control valve 80 can include any number of control valves that can quickly and accurately alter the flow rate of a gas across a relatively wide range of flow rates.

The output of the first control valve 80 leads to the oxygen-containing gas limb 62 of the patient 4. In this regard, the first control valve 80 controls the inspiration profile of the oxygen-containing gas 20. The inspiration profile of the oxygen-containing gas 20 is the flow rate of the oxygen-containing gas 20 as a function of inspiration time. The inspiration profile of the oxygen-containing gas 20 can be seen in FIGS. 7(*a*) and 7(*b*).

Still referring to FIG. 6, a second control valve 82 is located in-line between the NO-containing gas 22 and the NO-containing gas limb 64. The second control valve 82 thus receives the NO-containing gas 22 at an input port and modulates, or controls the flow of the NO-containing gas 22 into the NO-containing gas limb 64 through a second export port. The second control valve 82 can include, for example, a proportional control valve that opens (or closes) in a progressively increasing (or decreasing if closing) manner depending on an electronic input. As another example, the second control valve 82 can also include a mass flow controller. The second control valve 82 can include any number of control valves that can quickly and accurately alter the flow rate of a gas across a relatively wide range of flow rates. Like the first control valve 80, the inspiration profile of the second control valve 82 controls the inspiration profile of the NO-containing gas 22. The inspiration profile of the NO-containing gas 22 is the flow rate of the NO-containing gas 22 as a function of time.

The spontaneously breathing device 60 includes a CPU 84. The CPU 84 controls the first and second control valves 80, 82. The CPU 84 sends, via signal lines 86, 88, signals to control the opening and closing of the control valves 80, 82.

The device 60 further includes an inspiration flow profile sensor 90 that is positioned in the patient 4 breathing limb. Preferably, the inspiration flow profile sensor 90 is located downstream of the mixing point 66, but upstream of the patient inspiration interface device 70. In one aspect, the inspiration flow profile sensor 90 detects the flow rate of the inspired gas by the patient 4. The inspiration flow profile sensor 90 thus detects the onset of inspiration as well as the inspiration flow profile throughout the remainder of the breath. The flow profile sensor 90 can include any number of devices, including venturi-based sensor, hot wire anemometer, rotating vane, thermal flow, pressure transducer, and the like. Preferably, a flow profile sensor 90 is used that can rapidly detect small changes in the breathing flow rate over a wide range of flow rates.

In another aspect, the flow profile sensor 90 detects only the onset of inspiration by the patient 4.

The inspiration profile sensor 90 reports the inspiration flow rate data back to the CPU 84 via signal line 92 on preferably a real-time basis (or as close to a real-time basis as possible). The flow rate data reported back to the CPU 84 is the flow rate of the breathing gas (oxygen-containing gas 20 and NO-containing gas 22) as a function of time. This data represents the inspiration flow profile for each individual breath.

As an alternative to measuring the flow rate of the breathing gas as a function of time, the inspiration profile sensor 90 can just measure the onset of inspiration. The data reflecting the onset of inspiration is delivered as a signal to CPU 84. Pre-programmed flow profiles of the oxygen-containing gas 20 and the NO-containing gas 22 are then delivered to the patient 4. In general, the pre-programmed flow profiles of the oxygen-containing gas 20 and the NO-containing gas 22 are determined by empirical studies of patient inhalation characteristics. The flow profile of the oxygen-containing gas 20 and the NO-containing gas 22 can be proportional, quasi-proportional, or any other pre-determined flow pattern. This aspect is shown, for example, in FIG. 7(*c*).

Figure 7A:
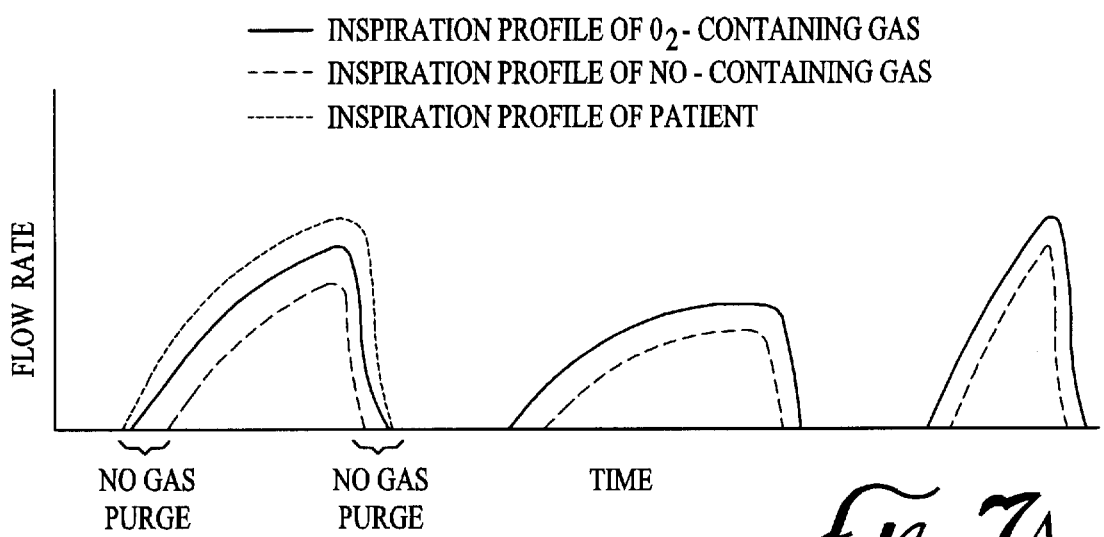
FIG. 7(a) illustrates a inspiration profile for a spontaneously breathing patient in addition to the flow profiles of the oxygen-containing gas and the NO-containing gas for delivering a constant concentration of NO to a patient.
Figure 7B:
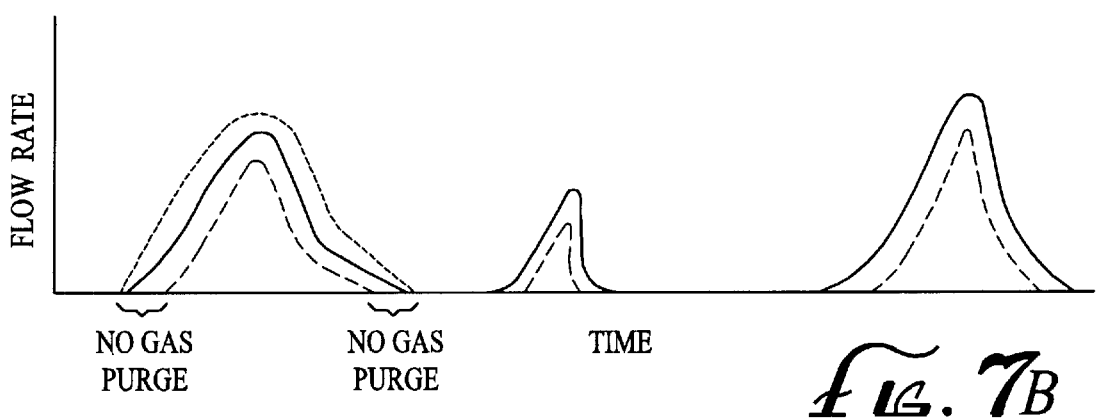
FIG. 7(b) illustrates another inspiration profile for a spontaneously breathing patient in addition to the flow profiles of the oxygen-containing gas and the NO-containing gas for delivering a constant concentration of NO to a patient.
Figure 7C:
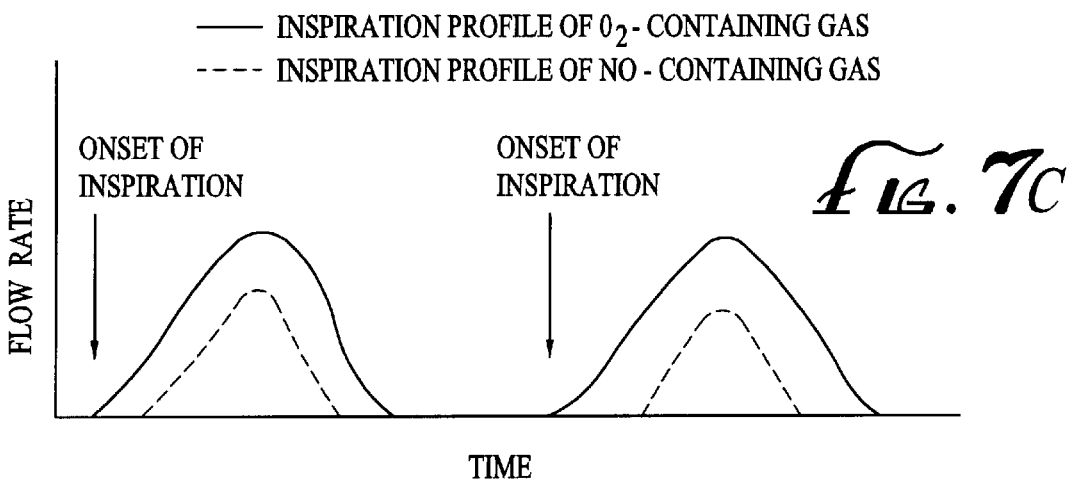
FIG. 7(c) illustrates pre-programmed inspiration profiles of the oxygen-containing gas and the NO-containing gas.

Based on the signal received from the inspiration profile sensor 90, the CPU 84 controls both the first and second control valves 80, 82 to delivery respective flow profiles of oxygen and NO. In one aspect of the invention, the CPU 84 contains instructions to deliver proportional flows of both the oxygen-containing gas 20 and the NO-containing gas 22. In this regard, a steady concentration of NO is delivered to the patient. This flow pattern is embodied in FIGS. 7(*a*) & 7(*b*). The dotted-line in FIG. 1 illustrates the inspiration flow profile of the patient 4. As can be seen in FIGS. 7(*a*) & 7(*b*), not only is the flow of the oxygen-containing gas 20 proportional to the inspirational flow of the patient 4, the flow of the NO-containing gas 22 is proportional to both the inspirational flow of the patient 4 as-well as the inspirational flow of the oxygen-containing gas 20.

The device 60 preferably includes an input device 94. The input device 94 can be any number of devices including, for example, a computer, diskette, control panel, and the like. The input device 94 can control, for example, the set-point concentration of NO in the breathing gas. The input device 94 can thus alter the degree of proportionality between the flow profile of the oxygen-containing gas 20 and the flow profile of the NO-containing gas 22. A higher degree of proportionality (i.e., the flow profile of the NO-containing gas 22 more closely tracks the flow profile of the oxygen-containing gas 20) would generally produce a higher concentration of inspired NO. The degree of proportionality also affects the timing of the NO gas purge.

The input device 94 may also input gas purge parameters to the CPU 84 to determine when the flow profile of the NO-containing gas 22 is truncated. This can be done, for example, by establishing a time after inspiration is started at which the flow profile of the NO-containing gas 22 is dropped to zero. Alternatively, the NO-containing gas 22 can terminate once the flow rate of the oxygen-containing gas 20 drops below a certain pre-set level. These settings can be input to the CPU 84 via the input device 94.

Still referring to FIGS. 7(*a*) & 7(*b*), the proportional flow of the NO-containing gas 22 also provides the device 60 and method with a purge feature to purge any NO gas from the lines and the patient inspiration interface device 70. At both the beginning and end of the patient's 4 inspiration, there is a positive flow of the oxygen-containing gas 20, while the flow of the NO-containing gas 22 is zero. Consequently, at the beginning and end of each breath, the device is purged on NO gas.

With respect to the spontaneous-breathing embodiment, the present invention also contemplates using a CPU 84 that gives the device 60 complete programmability. In this regard, the flow profiles of the both the oxygen-containing gas 20 and the NO-containing gas 22 can be controlled during a single breath. While proportional and quasi-proportional flow profiles are disclosed in greater detail herein, it should be appreciated that any flow profile (of the oxygen-containing gas 20 or the NO-containing gas 22) can be produced for a single breath of a MO patient 4. Complete programmability is also possible where the device employs input device 94.

While CPU 84 is shown as the preferred controller for controlling the flow profiles of the oxygen-containing gas 20 and the NO-containing gas 22, the present invention further contemplates using an analog switching mechanism (not shown) as an alternative controller.

The device 60 can further include an optional gas monitor 96. The gas monitor 96 preferably monitors the concentration of one or more of the following gases in the inspiration limb of the device 60: oxygen, NO, and $NO_2$. The gas monitor 96 determines the concentration of gas(es) via a sensor(s) 98 located in the inspiration limb. The sensor(s) 98 can be a chemilluminesence-type, electrochemical cell-type, or spectrophotometric-type sensor 98 based on the accuracy and response time desired. The gas monitor 96 preferably includes a display screen 100 that illustrates, on a real-time basis or as close to a real-time basis as possible, the concentrations of the measured gases.

Figure 8A:
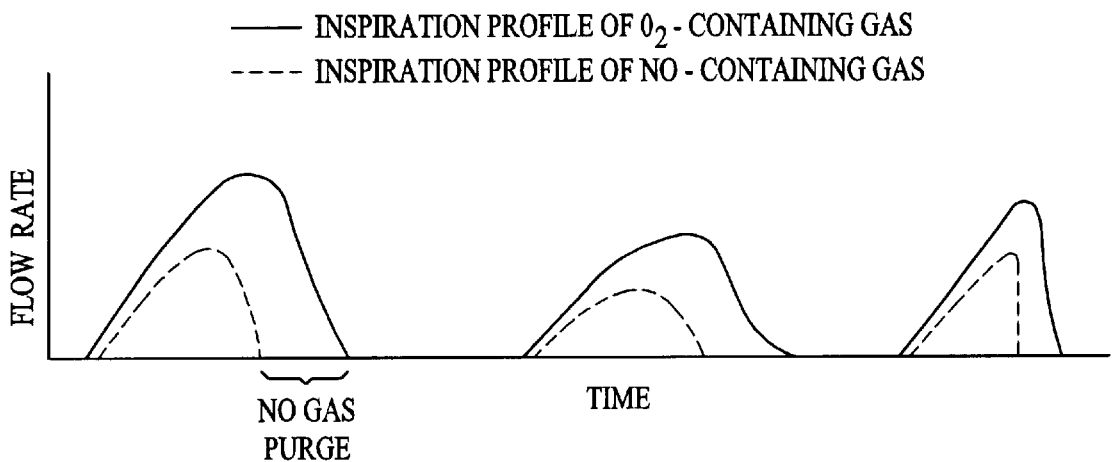
FIG. 8(a) illustrates an inspiration profile for the oxygen-containing gas and the NO-containing gas for delivering a non-constant concentration of NO to a patient, wherein the concentration of NO is higher at the beginning of inspiration than at the end of inspiration.
Figure 8B:
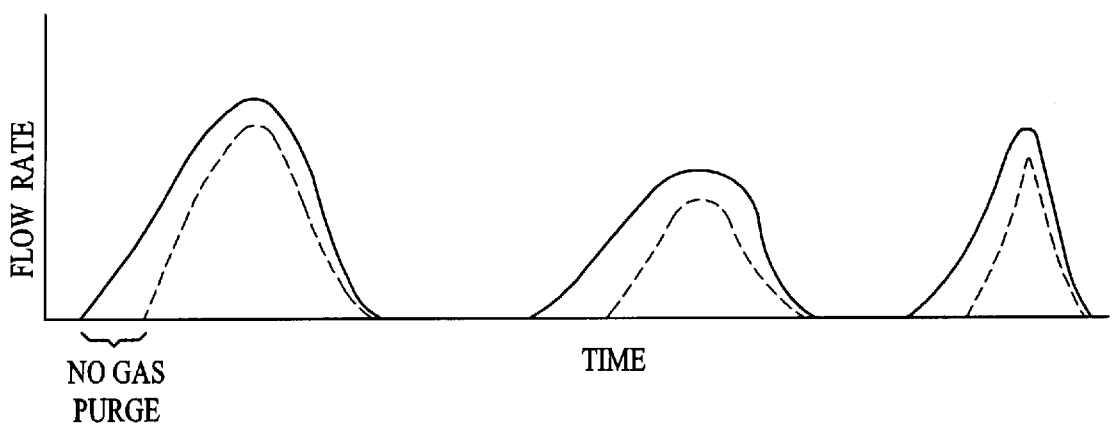
FIG. 8(b) illustrates another inspiration profile for the oxygen-containing gas and the NO-containing gas for delivering a non-constant concentration of NO to a patient, wherein the concentration of NO is higher at the end of inspiration than at the beginning of inspiration.

Referring now to FIG. 8(*a*), a separate aspect of the spontaneous-breathing device 60 will now be disclosed. In this aspect of the invention, a non-constant concentration of NO is delivered to the patient 4. In one aspect, the flow profile of the NO-containing gas 22 is such that a higher concentration of NO is delivered at the beginning of inspiration than the concentration delivered near the end of inspiration. In this aspect, the flow profile of the NO-containing gas 22 is less than flow profile of the oxygen-containing gas 20 and closely tracks the oxygen-containing gas 20 flow profile at the beginning of inspiration (quasi-proportional), but begins to tail-off as inspiration progresses. In this manner, the difference between the flow profiles of the oxygen-containing gas 20 and the NO-containing gas 22 progressively increases through the remainder of inspiration. This flow profile is used when it is desirous for NO to be delivered deep within the lungs, for instance, to treat pulmonary hypertension. This method of delivery, as stated previously, provides a gradual gradient of NO through the in the lungs rather than a bolus of NO that is disclosed in the '433 patent.

With respect to the flow profile shown in FIG. 8(*a*), and as stated previously, the difference between the flow profiles of the oxygen-containing gas 20 and the NO-containing gas 22 progressively increases through the remainder of inspiration. The rate of this increase, however, may be controlled by the CPU 84. For example, the increase may be linear, non-linear, exponential, etc., depending on the desired flow profile of the NO-containing gas 22. Further, the rate of this increase may be set by the input device 94.

This delivery method also contains gas purge feature that purges any NO gas from the lines and the patient inspiration interface device 70. At the end of the patient's 4 inspiration, there is a positive flow of the oxygen-containing gas 20, while the flow of the NO-containing gas 22 is zero. At this point in the patient's inspiration, the flow of oxygen-containing gas 20 purges the system of NO gas.

Referring now to FIG. 8(*b*), another flow profile is shown for the NO-containing gas 22 that provides for a greater NO concentration at the end portion of a patient's 4 inspiration. In this flow profile, the flow profile of the NO-containing gas 22 is substantially less than the oxygen-containing gas 20 flow profile. Most preferably, the flow profile of the NO-containing gas 22 starts out at zero, while the flow profile of the oxygen-containing gas 20 is positive The flow profile of the NO-containing gas 22 begins to more closely track the flow profile of the oxygen-containing gas 20, wherein the difference between the flow profile of the oxygen-containing gas 20 and the NO-containing gas 22 progressively decreases throughout the remainder of inspiration. In this flow profile, a higher concentration of NO is delivered to the upper airway region of the lungs. This method is used, as stated previously, in breathing diseases relating to broncho-construction of the airways, such as asthma.

With respect to the flow profile shown in FIG. 8(*b*), the difference between the flow profiles of the oxygen-containing gas 20 and the NO-containing gas 22 progressively decreases through the remainder of inspiration. The rate of this decrease, however, may be controlled by the CPU 84. For example, the decrease may be linear, non-linear, exponential, etc., depending on the desired flow profile of the NO-containing gas 22. Further, the rate of this decrease may be set by the input device 94.

This delivery method also contains gas purge feature that purges any NO gas from the lines and the patient inspiration interface device 70. At the beginning of the patient's 4 inspiration, there is a positive flow of the oxygen-containing gas 20, while the flow of the NO-containing gas 22 is zero. At this point in the patient's inspiration, the flow of oxygen-containing gas 20 purges the system of NO gas. Consequently, any remaining NO that might have remained in the lines and/or patient inspiration interface device 70 from the previous breath are purged by the flow of the oxygen-containing gas 20.

Figure 9A:
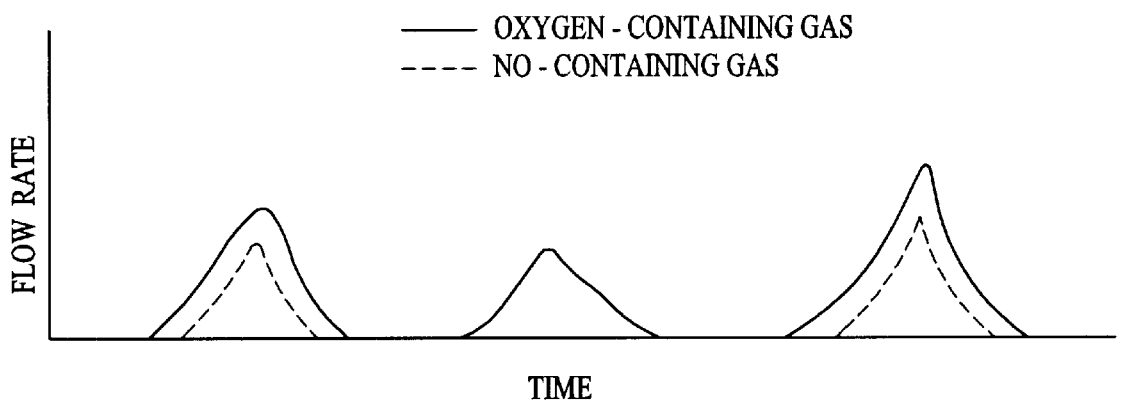
FIG. 9(a) is a flow profile of oxygen-containing gas and NO-containing gas where enriched-oxygen is delivered between breaths.
Figure 9B:
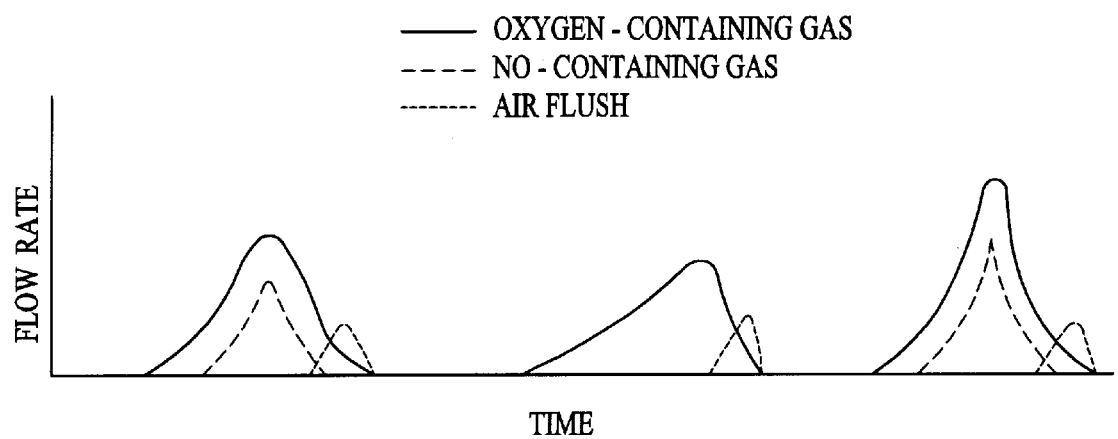
FIG. 9(b) shows the flow profile of the oxygen-containing gas, the NO-containing gas, and the air flush according to one aspect of the invention.

In another flow profile, shown in FIG. 9(*a*), a patient 4 receives a first inhalation containing both oxygen-containing gas 20 and NO-containing gas 22. In the next inhalation breath, the patient receives just oxygen-containing gas 20. Preferably, this inspiration contains a relatively high concentration of oxygen-containing gas 20 (oxygen-enriched). In the third inspiration, the patient 4 again receives an oxygen-containing gas 20 and an NO-containing gas 22. While the flow profile shown in FIG. 9(*a*) is show as alternating between oxygen-containing gas-only 20 and NO-containing gas 22 plus oxygen-containing gas 20, the profile could also include, for example, two or more oxygen-containing gas 22-only inspirations between inspirations having both oxygen-containing gas 20 and NO-containing gas 22.

Yet another flow profile is shown in FIG. 9(*b*). In FIG. 9(*b*), a patient 4 is delivered, on inspiration, a flow profile including an oxygen-containing gas 20 and a NO-containing gas 22. At or near the end of this inspiration, an air flush is delivered to the patient 4. The air flush serves to remove any NO-containing gas 22 that may be in the inspiration limb 8.

In the next inspiration, an oxygen-containing gas 20 is delivered to the patient 4-without any NO-containing gas 22. Preferably, the oxygen-containing gas 20 includes an elevated level of oxygen (enriched-oxygen). At or near the end of this inhalation, another air flush is delivered to the patient 4. This air flush is delivered to the patient 4 and serves to remove any enriched-oxygen gas remaining in the inspiration limb 8.

Figure 10:
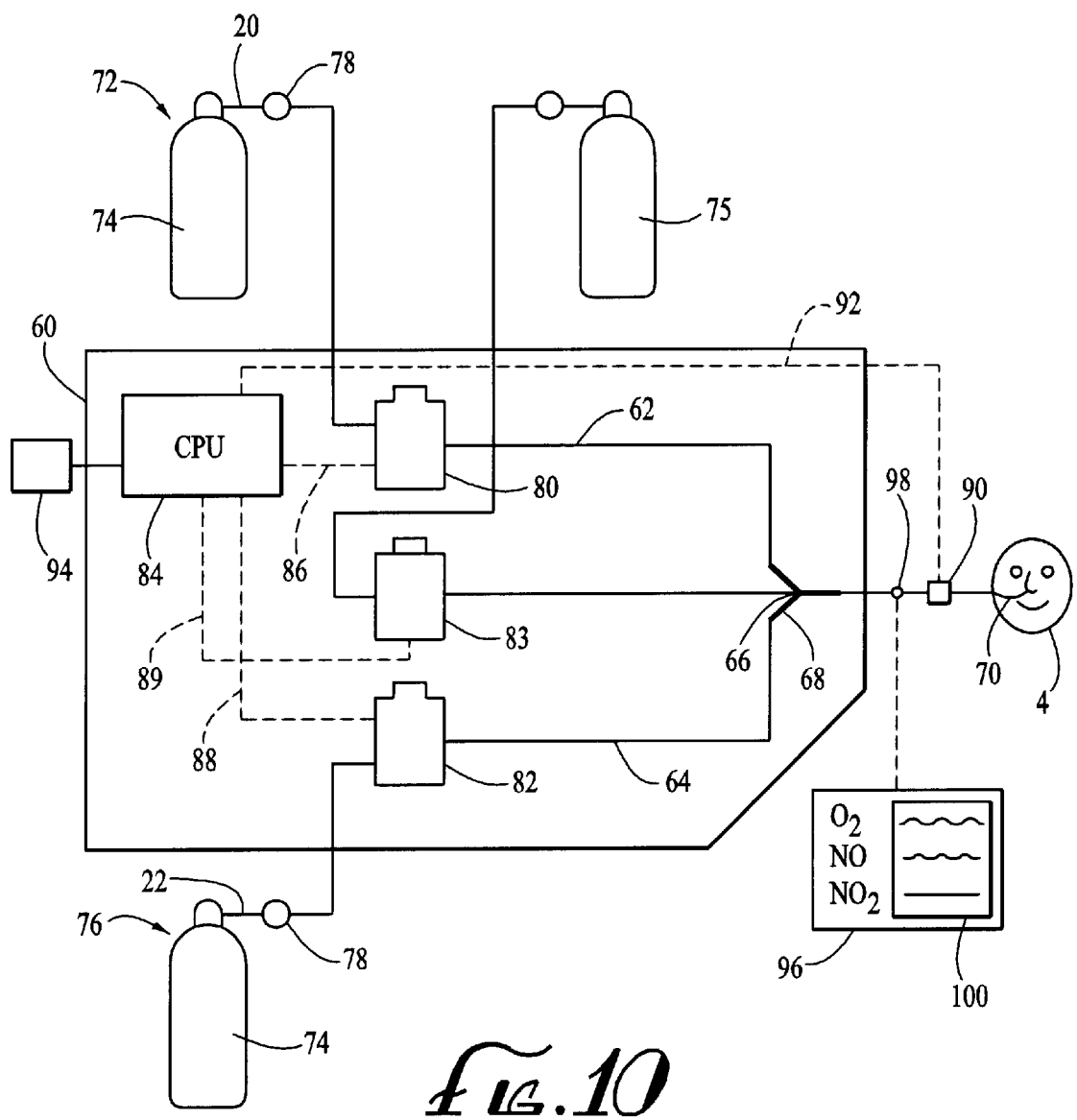
FIG. 10 is a schematic illustration of a device being used with a spontaneously-breathing patient wherein the air flush aspect is utilized.

In this embodiment, there are two separate sources of oxygen-containing gas 20. One source is the air used to flush the device 60 while the other source is the enriched-oxygen-containing gas 20. The source of air for the air flush can be, for example, a separate pressurized cylinder, wall supply, compressor, pump, or the like. FIG. 10, for example, shows the air being-stored in a pressurized cylinder 75 while the enriched oxygen-containing gas 20 enters the device via a wall supply or the like. The flow of air is modulated by a third control valve 83 that is controlled by the CPU 84 via signal line 89.

While embodiments of the present invention have been shown and described, various modifications may be made without departing from the scope of the present invention, and all such modifications and equivalents are intended to be covered.

What is claimed is:

1. A method of delivering a non-constant concentration of nitric oxide to a spontaneously breathing patient via delivery means comprising the steps of:
    detecting the onset of inspiration;
    determining an inspiration flow profile for an individual breath;
    supplying an oxygen-containing gas to the delivery means, the oxygen-containing gas having a flow profile determined based on the inspiration flow profile; and
    supplying an nitric oxide-containing gas to the delivery means, the nitric oxide-containing gas having a flow profile that is less than the oxygen-containing gas flow profile at the onset of inspiration, wherein the difference between the flow profile of the oxygen-containing gas and the flow profile of the nitric oxide-containing gas progressively increases throughout inspiration.

2. A method according to claim 1, further including the step of monitoring the concentration of one or more of the following gases prior to the delivery means: oxygen, nitric oxide, and nitrogen dioxide.

3. A method according to claim 1, wherein the flow profile of the nitric oxide-containing gas reaches zero flow at a time near the end of the patient inspiration flow profile, and wherein when said flow reaches zero, the flow profile of the oxygen-containing gas is greater than zero such that the oxygen-containing gas purges the inspiration limb of nitric oxide-containing gas.

4. A method according to claim 1, wherein the delivery means is a nasal cannula.

5. A method according to claim 1, wherein the delivery means is a face mask.

6. A method according to claim 1, wherein a delivery means is a transtracheal catheter.

7. A method of delivering a non-constant concentration of nitric oxide to a spontaneously breathing patient comprising the steps of:
    detecting the onset of inspiration;
    determining an inspiration flow profile for an individual breath;
    supplying an oxygen-containing gas to the delivery means, the oxygen-containing gas having a flow profile determined based on the inspiration profile; and
    supplying an nitric oxide-containing gas to the delivery means, the nitric oxide-containing gas having a flow profile that is less than the oxygen-containing gas flow profile at the onset of inspiration compared to the end of inspiration, and wherein the difference between the flow profile of the oxygen-containing gas and the flow profile of the nitric oxide-containing gas progressively decreases throughout inspiration.

8. A method according to claim 7, wherein the method further includes the step of monitoring the concentration of one or more of the following gases prior to the delivery means: oxygen, nitric oxide, and nitrogen dioxide.

9. A method according to claim 7, wherein the flow profile of the nitric oxide-containing gas is zero at the beginning of inspiration and the flow profile of the oxygen-containing gas is positive.

10. A method according to claim 7, wherein the delivery means is a nasal cannula.

11. A method according to claim 7, wherein the delivery means is a face mask.

12. A method according to claim 7, wherein the delivery means is a transtracheal catheter.

13. A method of delivering a constant concentration of nitric oxide to a mechanically-ventilated patient via single controller using a mechanical ventilator, the mechanical ventilator having an inspiration limb and an expiration limb, the method comprising the steps of:
    setting a desired inspiration flow profile in the controller;
    varying a flow rate of an oxygen-containing gas in accordance with the inspiration flow profile by delivering a first signal from said controller to a first control valve controlling the rate of flow of an oxygen-containing gas to the patient, thereby creating a flow profile of oxygen-containing gas; and
    varying a flow rate of a nitric oxide-containing gas in accordance with the inspiration profile by delivering a second signal from said controller to a second control valve controlling the rate of flow of the nitric oxide-containing gas to the patient, creating a flow profile of nitric oxide-containing gas, said flow profile of the nitric oxide-containing gas being proportionally less than the flow profile of the oxygen-containing gas throughout patient inspiration.

14. A method according to claim 13, wherein the flow profile of the nitric oxide-containing gas reaches zero flow at a time near the end of the patient inspiration flow profile, and wherein the flow profile of the oxygen-containing gas is greater than zero such that the oxygen-containing gas purges the inspiration limb of nitric oxide-containing gas.

15. A method according to claim 13, wherein the flow profile of the nitric oxide-containing gas is zero flow at the beginning of the patient inspiration flow profile, and wherein when said flow is zero, the flow profile of the oxygen-containing gas is greater than zero such that the oxygen-containing gas purges the inspiration limb of nitric oxide-containing gas.

16. A method according to claim 13, wherein the flow profile of the nitric oxide-containing gas is zero at the beginning of the patient inspiration profile while the flow profile of the oxygen-containing gas is greater than zero, and wherein at a time near the end of the patient inspiration flow profile the flow profile of the nitric oxide-containing gas is zero while the flow profile of the oxygen-containing gas is greater than zero, wherein when the nitric oxide-containing gas flow reaches zero and the flow profile of the oxygen-containing gas is greater than zero the oxygen-containing gas purges the inspiration limb of nitric oxide-containing gas.

17. A method according to claim 13, further including the step of monitoring the concentration of one or more of the following gases in the inspiration limb: oxygen, nitric oxide, and nitrogen dioxide.

18. A method according to claim 13, further comprising the step of truncating the flow profile of the nitric oxide-containing gas to zero near the end of patient inspiration.

19. A method of delivering a non-constant concentration of nitric oxide to a mechanically-ventilated patient via single controller using a mechanical ventilator, the mechanical ventilator having an inspiration limb and an expiration limb, the method comprising the steps of:

setting a desired inspiration flow profile in the controller;

varying a flow rate of an oxygen-containing gas in accordance with the inspiration flow profile by delivering a first signal from said controller to a first control valve controlling the rate of flow of an oxygen-containing gas to the patient, thereby creating a flow profile of oxygen-containing gas; and varying a flow rate of a nitric oxide-containing gas in accordance with the inspiration profile by delivering a second signal from said controller to a second control valve controlling the rate of flow of the nitric oxide-containing gas to the patient, creating a flow profile of nitric oxide-containing gas that is less than the oxygen-containing gas flow profile in the onset of inspiration, wherein the difference between the flow profiles of the oxygen-containing gas and the nitric oxide-containing gas progressively increases throughout inspiration.

20. A method according to claim 19, wherein the flow profile of the nitric oxide-containing gas reaches zero flow at a time near the end of the patient inspiration flow profile, and wherein when said flow reaches zero, the flow profile of the oxygen-containing gas is greater than zero such that the oxygen-containing gas purges the inspiration limb of nitric oxide-containing gas.

21. A method of delivering a non-constant concentration of nitric oxide to a mechanically-ventilated patient via single controller using a mechanical ventilator, the mechanical ventilator having an inspiration limb and an expiration limb, the method comprising the steps of:

setting a desired inspiration flow profile in the controller;

varying a flow rate of an oxygen-containing gas in accordance with the inspiration flow profile by delivering a first signal from said controller to a first control valve controlling the rate of flow of an oxygen-containing gas to the patient, thereby creating a flow profile of oxygen-containing gas; and varying a flow rate of a nitric oxide-containing gas in accordance with the inspiration profile by delivering a second signal from said controller to a second control valve controlling the rate of flow of the nitric oxide-containing gas to the patient, the nitric oxide-containing gas having a flow profile that is less than the oxygen-containing gas flow profile at the beginning of inspiration, and wherein the difference between the flow profile of the oxygen-containing gas and the nitric oxide-containing gas progressively decreases throughout inspiration.

22. A method according to claim 21, wherein the flow profile of the nitric oxide-containing gas is zero at the beginning of inspiration and the flow profile of the oxygen-containing gas is positive.

23. A method according to claim 21, further including the step of monitoring the concentration of one or more of the following gases in the inspiration limb: oxygen, nitric oxide, and nitrogen dioxide.

24. A method of delivering a steady concentration of nitric oxide to a spontaneously breathing patient via delivery means having an inspiration limb comprising the steps of:

detecting the onset of inspiration;

determining an inspiration flow profile for an individual breath;

supplying an oxygen-containing gas to the delivery means, the oxygen-containing gas having a flow profile determined based on the inspiration flow profile;

supplying an nitric oxide-containing gas to the delivery means, the nitric oxide-containing gas having a flow profile that is proportionally less than the flow profile of the oxygen-containing gas throughout inspiration; and wherein the flow profile of the nitric oxide-containing gas reaches zero flow at a time near the end of the patient inspiration flow profile, and wherein when said flow reaches zero, the flow profile of the oxygen-containing gas is greater than zero such that the oxygen-containing gas purges the inspiration limb of nitric oxide-containing gas.

25. A method of delivering a steady concentration of nitric oxide to a spontaneously breathing patient via delivery means having an inspiration limb comprising the steps of:

detecting the onset of inspiration;

determining an inspiration flow profile for an individual breath;

supplying an oxygen-containing gas to the delivery means, the oxygen-containing gas having a flow profile determined based on the inspiration flow profile;

supplying an nitric oxide-containing gas to the delivery means, the nitric oxide-containing gas having a flow profile that is proportionally less than the flow profile of the oxygen-containing gas throughout inspiration; and wherein the flow profile of the nitric oxide-containing gas is zero flow at the beginning of the patient inspiration flow profile, and wherein when said flow is zero, the flow profile of the oxygen-containing gas is greater than zero such that the oxygen-containing gas purges the inspiration limb of nitric oxide-containing gas.

26. A method of delivering a steady concentration of nitric oxide to a spontaneously breathing patient via delivery means having an inspiration limb comprising the steps of:

detecting the onset of inspiration;

determining an inspiration flow profile for an individual breath;

supplying an oxygen-containing gas to the delivery means, the oxygen-containing gas having a flow profile determined based on the inspiration flow profile;

supplying an nitric oxide-containing gas to the delivery means, the nitric oxide-containing gas having a flow profile that is proportionally less than the flow profile of the oxygen-containing gas throughout inspiration; and wherein the flow profile of the nitric oxide-containing gas is zero at the beginning of the patient inspiration profile while the flow profile of the oxygen-containing gas is greater than zero, and wherein at a time near the end of the patient inspiration flow profile, the flow profile of the nitric oxide-containing gas is zero while the flow profile of the oxygen-containing gas is greater than zero, wherein when the nitric oxide-containing gas flow reaches zero and the flow profile of the oxygen-containing gas is greater than zero the oxygen-containing gas purges the inspiration limb of nitric oxide-containing gas.

* * * * *